US012745925B2

(12) United States Patent
Kajitani

(10) Patent No.: US 12,745,925 B2
(45) Date of Patent: Sep. 29, 2026

(54) GAIT INFORMATION GENERATION DEVICE, GAIT MEASUREMENT SYSTEM, GAIT INFORMATION GENERATION METHOD, AND RECORDING MEDIUM

(71) Applicant: NEC Corporation, Tokyo (JP)

(72) Inventor: Hiroshi Kajitani, Tokyo (JP)

(73) Assignee: NEC CORPORATION, Tokyo (JP)

( * ) Notice: Subject to any disclaimer, the term of this patent is extended or adjusted under 35 U.S.C. 154(b) by 270 days.

(21) Appl. No.: 18/595,537

(22) Filed: Mar. 5, 2024

(65) Prior Publication Data

US 2024/0315600 A1 Sep. 26, 2024

(30) Foreign Application Priority Data

Mar. 23, 2023 (JP) ................................ 2023-046778

(51) Int. Cl.
*A61B 5/11* (2006.01)
*A61B 5/00* (2006.01)

(52) U.S. Cl.
CPC ............ *A61B 5/112* (2013.01); *A61B 5/6807* (2013.01); *A61B 5/7264* (2013.01); *A61B 2562/0219* (2013.01)

(58) Field of Classification Search
CPC ...... A61B 5/112; A61B 5/6807; A61B 5/7264
See application file for complete search history.

(56) References Cited

U.S. PATENT DOCUMENTS

2002/0040601 A1* 4/2002 Fyfe .................. A63B 69/0028 73/488
2008/0146968 A1* 6/2008 Hanawaka ........... A61B 5/0002 600/595
2017/0273616 A1* 9/2017 Yang ...................... A61B 5/486
2019/0150793 A1* 5/2019 Barth ..................... A61B 5/112
2021/0298602 A1* 9/2021 Hirata .................... G16H 40/63
2022/0218233 A1* 7/2022 Huang .................. A61B 5/112

FOREIGN PATENT DOCUMENTS

JP 6307673 B 4/2018

* cited by examiner

*Primary Examiner* — Daniel L Cerioni

(57) ABSTRACT

A gait information generation device includes a communication unit that acquires sensor data measured in response to a motion of a foot, an increment calculating unit that calculates an increment of a lateral distance by using lateral acceleration included in the sensor data, a gait information generating unit that calculates, as a step width, a sum of a heel center distance substantially equivalent to a distance between center lines of heels of both feet in an initial state and a sum total of the increments of the lateral distance, and generates gait information related to the calculated step width, and an output unit that outputs the generated gait information.

10 Claims, 21 Drawing Sheets

GAIT INFORMATION GENERATION DEVICE, GAIT MEASUREMENT SYSTEM, GAIT INFORMATION GENERATION METHOD, AND RECORDING MEDIUM

This application is based upon and claims the benefit of priority from Japanese Patent Application No. 2023-046778, filed on Mar. 23, 2023, the disclosure of which is incorporated herein in its entirety by reference.

TECHNICAL FIELD

The present disclosure relates to a gait information generation device, a gait measurement system, a gait information generation method, and a recording medium.

BACKGROUND ART

With growing interest in healthcare, services for measuring gait including features of gait and providing a user with information associated with the measured gait have attracted public attention. If gait parameters such as a step width, a step length, and a step angle can be detected from data related to gait, it is possible to provide a service according to gait. For example, a step width that is one of the gait parameters is an index of a state of a pedestrian. Therefore, if it is possible to measure a step width in daily gait, there is a possibility that an appropriate service according to a state of a pedestrian can be provided.

In general, the step width is measured using a floor embedded type force plate. The force plate is expensive and requires construction for sufficient floor strength. Although there is an inexpensive simple force plate, it is difficult to secure a distance for measuring a step width, and thus it is difficult to stably measure a step width. It is possible to measure a step width using a camera. In a case in which a camera is used, it is necessary to perform correction using images captured by a plurality of cameras. That is, similarly to the force plate, even if the camera is used, it is possible to measure a step width only in a specific environment.

PTL 1 (JP 6307673 B1) discloses a system that measures an interval between two limbs during walking or running. PTL 1 discloses an example of measuring an interval between two limbs (also referred to as a distance between both feet) using a non-contact interval measuring instrument employing an ultrasonic wave.

In the technique of PTL 1, an ultrasonic wave emitted from an ultrasonic wave transmitting unit installed on one foot is received by a receiving unit installed on the other foot, and a distance between both feet is calculated based on a propagation time of the ultrasonic wave. According to the technique of PTL 1, the distance between the ultrasonic wave transmitting unit installed on one foot and the receiving unit installed on the other foot can be measured as the distance between both feet during walking or running. However, in the technique of PTL 1, although the distance between both feet during walking or running can be measured, it is difficult to measure the step width. In the technique of PTL 1, it is necessary to use a non-contact type interval measuring instrument using an ultrasonic wave in the measurement of the distance between both feet.

It is an object of the present disclosure to provide a gait information generation device and the like capable of generating gait information related to a step width with a simple configuration.

SUMMARY

A gait information generation device according to one aspect of the present disclosure includes a communication unit that acquires sensor data measured in response to a motion of a foot, an increment calculating unit that calculates an increment of a lateral distance by using lateral acceleration included in the sensor data, a gait information generating unit that calculates, as a step width, a sum of a heel center distance substantially equivalent to a distance between center lines of heels of both feet in an initial state and a sum total of the increments of the lateral distance, and generates gait information related to the calculated step width, and an output unit that outputs the generated gait information.

A gait information generation method according to one aspect of the present disclosure causes a computer to execute acquiring sensor data measured in response to a motion of a foot, calculating an increment of a lateral distance by using lateral acceleration included in the sensor data, calculating, as a step width, a sum of a heel center distance substantially equivalent to a distance between center lines of heels of both feet and a sum total of the increments of the lateral distance, generating gait information related to the calculated step width, and outputting the generated gait information.

A program according to one aspect of the present disclosure causes a computer to execute a process of acquiring sensor data measured in response to a motion of a foot, a process of calculating an increment of a lateral distance by using lateral acceleration included in the sensor data, a process of calculating, as a step width, a sum of a heel center distance substantially equivalent to a distance between center lines of heels of both feet and a sum total of the increments of the lateral distance, a process of generating gait information related to the calculated step width, and a process of outputting the generated gait information.

BRIEF DESCRIPTION OF THE DRAWINGS

Exemplary features and advantages of the present invention will become apparent from the following detailed description when taken with the accompanying drawings in which.

EXAMPLE EMBODIMENT

Figure 1:
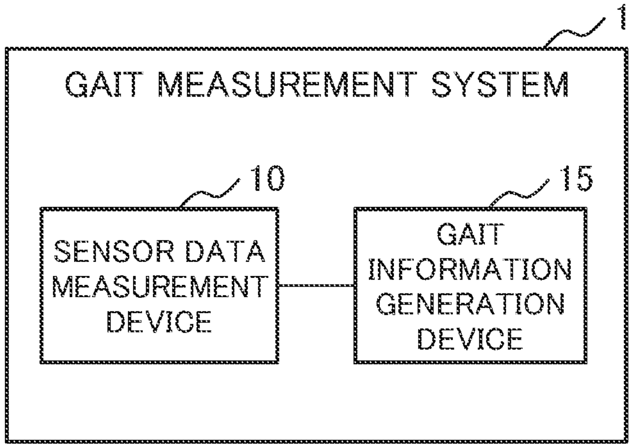
FIG. 1 is a block diagram illustrating an example of a configuration of a gait measurement system according to the present disclosure.

Example embodiments of the present invention will be described below with reference to the drawings. In the following example embodiments, technically preferable limitations are imposed to carry out the present invention, but the scope of this invention is not limited to the following description. In all drawings used to describe the following example embodiments, the same reference numerals denote similar parts unless otherwise specified. In addition, in the following example embodiments, a repetitive description of similar configurations or arrangements and operations may be omitted.

First Example Embodiment

First, a gait measurement system according to a first example embodiment will be described with reference to the drawings. The gait measurement system of the present example embodiment measures sensor data associated with gait of a user. The gait measurement system of the present example embodiment calculates a step width of the user using the measured sensor data.

Configuration

FIG. 1 is a block diagram illustrating an example of a configuration of a gait measurement system 1 according to the present example embodiment. The gait measurement system 1 includes a sensor data measurement device 10 and a gait information generation device 15. The sensor data measurement device 10 is installed on footwear or the like of a subject (user) who is a measurement target for the step width. For example, functions of the gait information generation device 15 are installed in a mobile terminal carried by the subject. The functions of the gait information generation device 15 may be implemented in a server or a cloud connected to a mobile terminal carried by the subject via a communication network. Hereinafter, a configuration of the sensor data measurement device 10 and the gait information generation device 15 will be individually described.

Sensor Data Measurement Device

Figure 2:
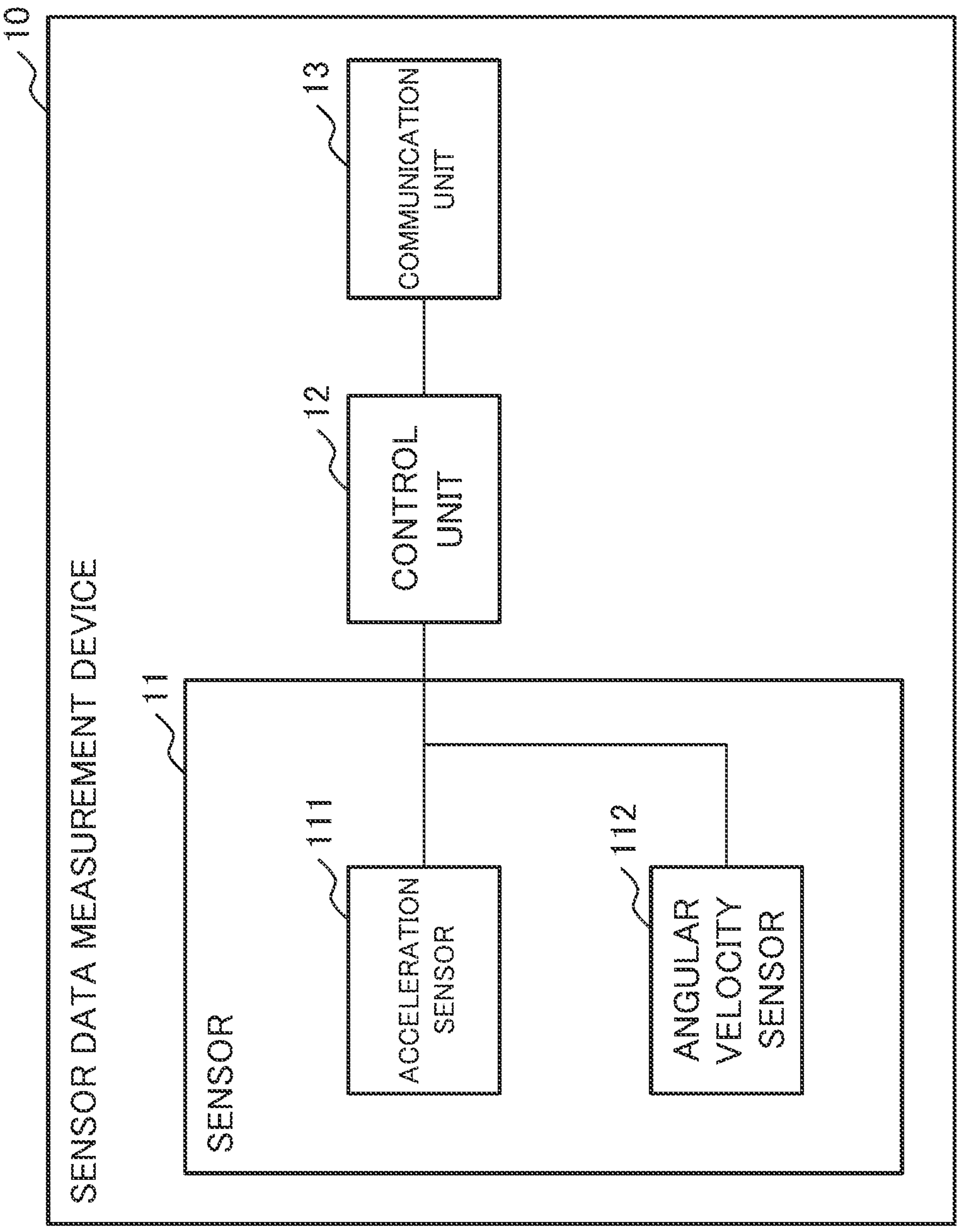
FIG. 2 is a block diagram illustrating an example of a configuration of a sensor data measurement device included in a gait measurement system according to the present disclosure.

FIG. 2 is a block diagram illustrating an example of a configuration of the sensor data measurement device 10. The sensor data measurement device 10 includes a sensor 11, a control unit 12, and a communication unit 13. As illustrated in FIG. 2, the sensor 11 includes an acceleration sensor 111 and an angular velocity sensor 112. FIG. 2 illustrates an example in which the acceleration sensor 111 and the angular velocity sensor 112 are included in the sensor 11. The sensor 11 may include a sensor other than the acceleration sensor 111 and the angular velocity sensor 112. The sensor other than the acceleration sensor 111 and the angular velocity sensor 112 which may be included in the sensor 11 will not be described.

The acceleration sensor 111 is a sensor that measures acceleration (also referred to as spatial acceleration) in three axial directions. The acceleration sensor 111 measures acceleration (also referred to as spatial acceleration) as a physical quantity related to motion of a foot. The acceleration sensor 111 outputs the measured acceleration to the control unit 12. For example, a sensor of a piezoelectric sensor, a piezoresistive sensor, a capacitive sensor, or the like can be used as the acceleration sensor 111. Any sensor capable of measuring acceleration can be used as the sensor used as the acceleration sensor 111.

The angular velocity sensor 112 is a sensor that measures angular velocity (also referred to as spatial angular velocity) around three axes. The angular velocity sensor 112 measures angular velocity (also referred to as spatial angular velocity) as a physical quantity related to motion of a foot. Angular velocity sensor 112 outputs the measured angular velocity to the control unit 12. For example, a sensor of a vibration sensor, a capacitive sensor, or the like can be used as the angular velocity sensor 112. Any sensor capable of measuring angular velocity can be used as the sensor used as the angular velocity sensor 112.

The sensor 11 is implemented by, for example, an inertial measurement device that measures acceleration or angular velocity. An example of the inertial measurement unit is an inertial measurement unit (IMU). The IMU includes the acceleration sensor 111 that measures acceleration in three axial directions and the angular velocity sensor 112 that measures angular velocities around the three axes. The sensor 11 may be implemented by an inertial measurement device such as a vertical gyro (VG) or an attitude heading reference system (AHRS). The sensor 11 may be implemented by global positioning system/inertial navigation system (GPS/INS). The sensor 11 may be implemented by a device other than the inertial measurement device as long as a physical quantity related to motion of a foot can be measured.

Figure 3:
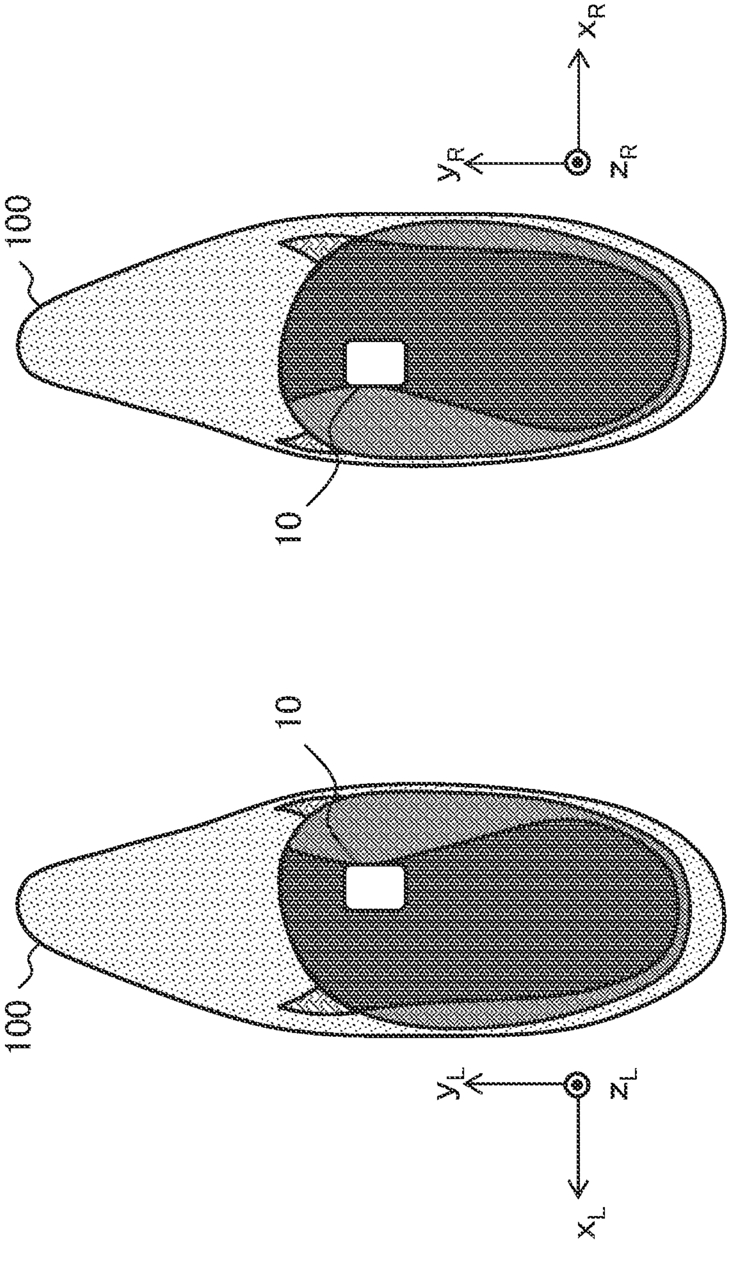
FIG. 3 is a conceptual diagram illustrating an arrangement example of a sensor data measurement device included in a gait measurement system according to the present disclosure.

FIG. 3 is a conceptual diagram illustrating an example in which the sensor data measurement devices 10 are arranged in shoes 100 of both feet. In the example of FIG. 3, the sensor data measurement device 10 is installed at a position associated with the back side of the arch of foot. For example, the sensor data measurement device 10 is arranged in an insole inserted into the shoe 100. For example, the sensor data measurement device 10 may be arranged on the bottom surface of the shoe 100. For example, the sensor data measurement device 10 may be embedded in the main body of the shoe 100. The sensor data measurement device 10 may be detachable from the shoe 100 or may be non-detachable from the shoe 100. The sensor data measurement device may be installed at a position other than the back side of the arch of foot as long as the sensor data related to the motion of the foot can be measured. The sensor data measurement device 10 may be installed on a sock worn by the user or a decorative article such as an anklet worn by the user. The sensor data measurement device 10 may be directly attached to the foot or may be embedded in the foot.

In the example of FIG. 3, a local coordinate system including an x-axis in a left-right direction, a y-axis in a front-rear direction, and a z-axis in an up-down direction is set with reference to the sensor data measurement device 10 (the sensor 11). FIG. 3 illustrates an example in which different coordinate systems are set for the left foot and the right foot. For the left foot, the left side is positive in the x-axis, the front side is positive in the y-axis, and the upper side is positive in the z-axis. For the right foot, the right side is positive in the x-axis, the front side is positive in the y-axis, and the upper side is positive in the z-axis. The directions of the axes set in the sensor 11 may be the same for the left and right feet. For example, in a case in which the sensors 11 produced with the same specifications are arranged in the left and right shoes 100, the vertical directions (the directions of the Z-axis direction) of the sensors 11 arranged in the left and right shoes 100 are the same direction. In this case, the three axes of the local coordinate system set in the sensor data derived from the left foot and the three axes of the local coordinate system set in the sensor data derived from the right foot are identical to each other in the left and right.

Figure 4:
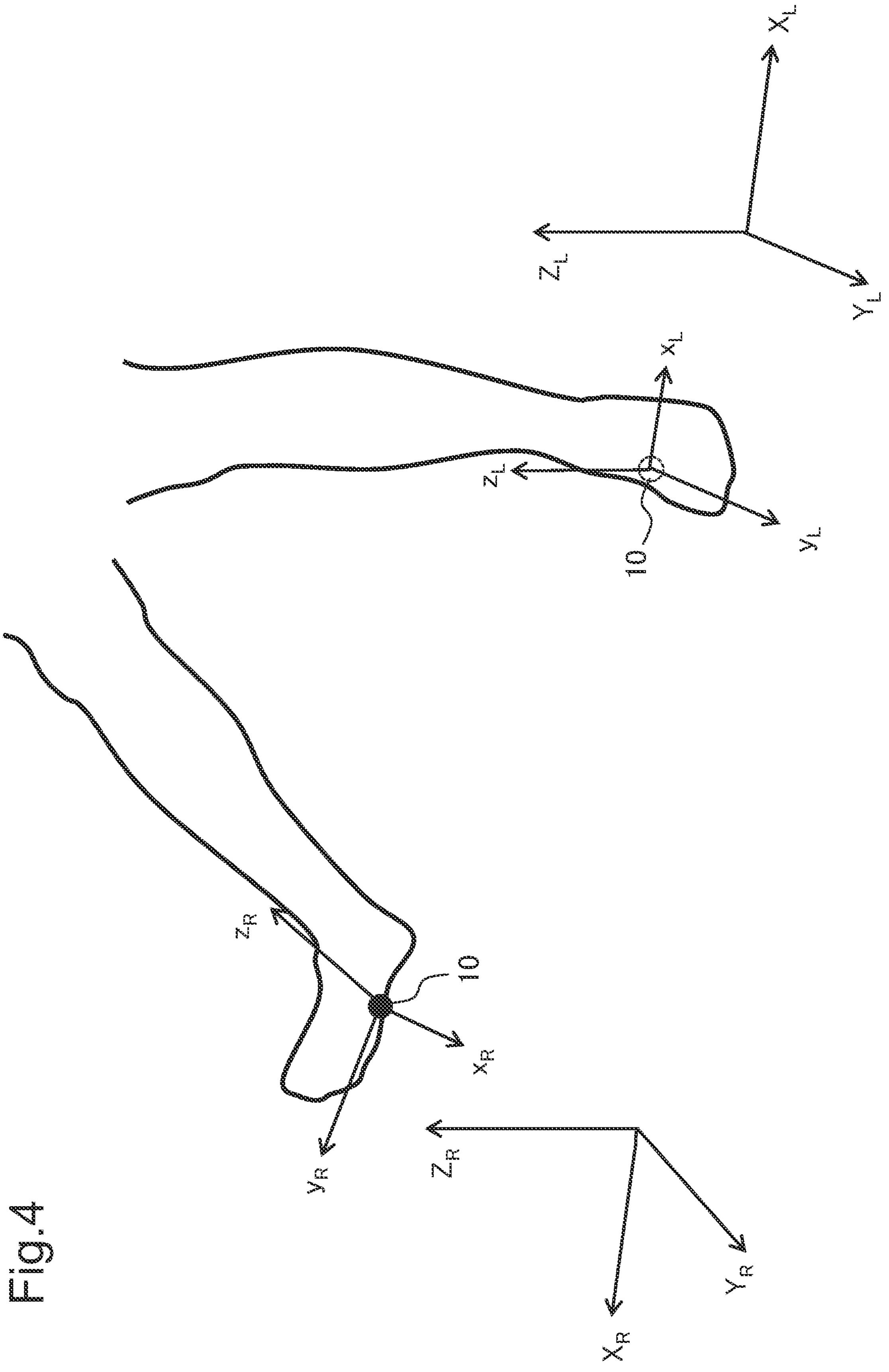
FIG. 4 is a conceptual diagram for explaining a coordinate system set in a sensor data measurement device included in a gait measurement system according to the present disclosure.

FIG. 4 is a conceptual diagram for explaining a local coordinate system (an x-axis, a y-axis, and a z-axis) set in the sensor data measurement device 10 (the sensor 11) installed on the back side of the arch of the foot and a world coordinate system (an X-axis, a Y-axis, and a Z-axis) set with respect to the ground surface. FIG. 4 illustrates an example in which different coordinate systems are set for the left foot and the right foot. In the world coordinate system (the X-axis, the Y-axis, and the Z-axis), in a state in which the user faces in a traveling direction, the lateral direction of the user is set as the X-axis direction, the direction of the back surface of the user is set as the Y-axis direction, and the gravity direction is set as the Z-axis direction. The example of FIG. 4 conceptually illustrates the relationship between the local coordinate system (the x-axis, the y-axis, and the z-axis) and the world coordinate system (the X-axis, the Y-axis, and the Z-axis), and does not accurately illustrate the relationship between the local coordinate system and the world coordinate system, which varies depending on the gait of the user.

Figure 5:
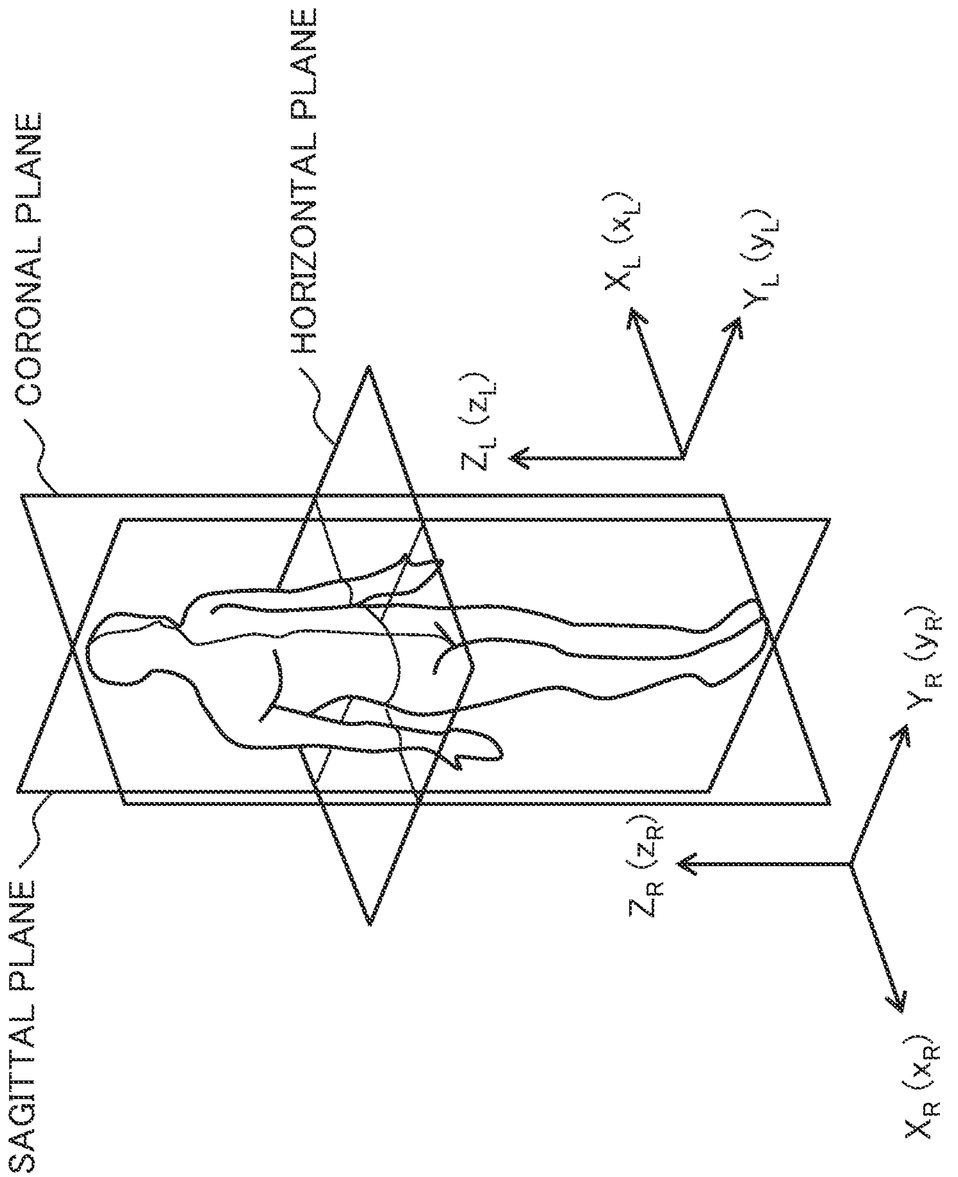
FIG. 5 is a conceptual diagram for explaining human body planes related to a gait measurement system according to the present disclosure.

FIG. 5 is a conceptual diagram for explaining planes (also referred to as human body planes) set for the human body. In the present example embodiment, a sagittal plane dividing the body into left and right, a coronal plane dividing the body into front and rear, and a horizontal plane dividing the body horizontally are defined. As illustrated in FIG. 5, it is assumed that the world coordinate system and the local coordinate system coincide with each other in a state in which the center line of the foot is oriented in the traveling direction. FIG. 5 illustrates an example in which different coordinate systems are set for the left foot and the right foot. In the present example embodiment, rotation of the sagittal plane with the X-axis (the x-axis) as the rotation axis is defined as a roll, rotation of the coronal plane with the Y-axis (the y-axis) as the rotation axis is defined as a pitch, and rotation of the horizontal plane with the Z-axis (the z-axis) as the rotation axis is defined as a yaw. A rotation angle of the sagittal plane with the X-axis (the x-axis) as the rotation axis is defined as a roll angle, the rotation angle of the coronal plane with the Y-axis (the y-axis) as the rotation axis is defined as a pitch angle, and the rotation angle of the horizontal plane with the Z-axis (the z-axis) as a rotation axis is defined as a yaw angle.

The control unit 12 (control means) acquires a measurement start signal transmitted from the gait information generation device 15 from the communication unit 13. The control unit 12 causes the acceleration sensor 111 and the angular velocity sensor 112 to start measurement in response to the measurement start signal. For example, the control unit 12 may cause the acceleration sensor 111 and the angular velocity sensor 112 to start measurement in response to detection of the gait of the user. For example, the control unit 12 may be configured to start the measurement of the step width at a point of time, as a starting point, at which motion of one of the right and left feet in the traveling direction is detected after the heights of both feet in the vertical direction become identical to each other over a predetermined period set in advance. The control unit 12 may be configured to start the measurement of the step width at a predetermined timing set in advance.

The control unit 12 acquires accelerations in three axial directions from the acceleration sensor 111. The control unit 12 acquires angular velocities around three axes from the angular velocity sensor 112. For example, the control unit 12 performs analog-to-digital conversion (AD conversion) on the acquired physical quantities (analog data) such as the angular velocities and the accelerations. The physical quantities (analog data) measured by the acceleration sensor 111 and the angular velocity sensor 112 may be converted into digital data in each of the acceleration sensor 111 and the angular velocity sensor 112. The control unit 12 outputs the converted digital data (also referred to as sensor data) to the communication unit 13.

The control unit 12 may be configured to store the sensor data in a storage unit (not illustrated). The sensor data includes at least acceleration data converted into digital data and angular velocity data converted into digital data. The acceleration data includes acceleration vectors in the three axial directions. The angular velocity data includes angular velocity vectors around the three axes. The acceleration data and the angular velocity data are associated with acquisition times of the data. The control unit 12 may add corrections such as a mounting error, temperature correction, and linearity correction to the acceleration data and the angular velocity data.

For example, the control unit 12 is implemented by a microcomputer or a microcontroller that performs overall control and data processing of the sensor data measurement device 10. For example, the control unit 12 includes a central processing unit (CPU), a random access memory (RAM), a read only memory (ROM), a flash memory, and the like. The control unit 12 controls the acceleration sensor 111 and the angular velocity sensor 112 such that the angular velocity and the acceleration are measured.

Figure 6:
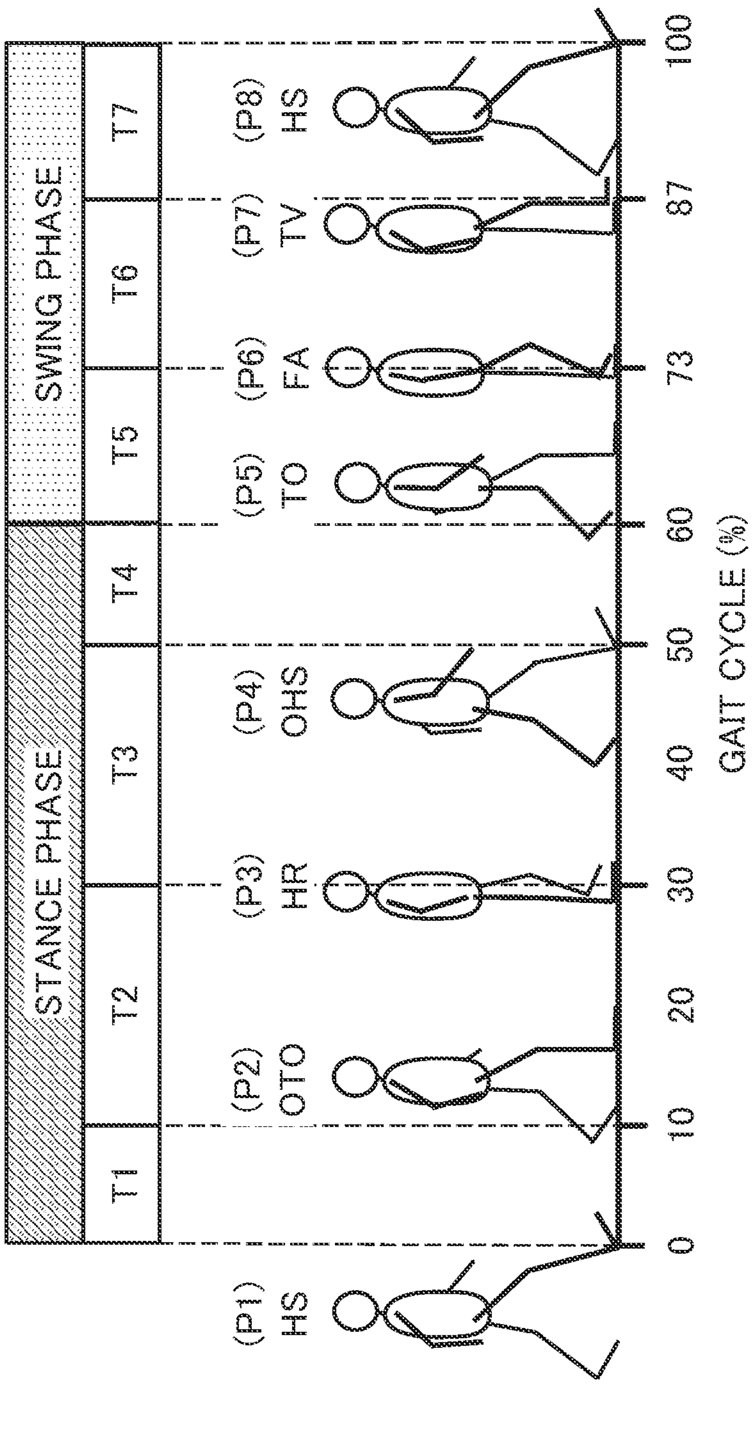
FIG. 6 is a conceptual diagram for explaining a gait cycle related to a gait measurement system according to the present disclosure.

FIG. 6 is a conceptual diagram for explaining one gait cycle based on the right foot. One gait cycle based on the left foot is also similar to that of the right foot. A horizontal axis of FIG. 6 indicates one gait cycle of the right foot in which a point of time at which the heel of the right foot touches the ground surface is a starting point and a point of time at which the heel of the right foot touches the ground surface again is an ending point. The horizontal axis in FIG. 6 is normalized by first normalization in which one gait cycle is set as 100%. The horizontal axis of FIG. 6 is normalized by second normalization in which a stance phase is set to take up 60% and a swing phase is set to take up 40%. One gait cycle of one foot is roughly divided into a stance phase in which at least a part of the back side of the foot is in contact with the ground surface and a swing phase in which the back side of the foot is separated from the ground surface. The stance phase is further subdivided into an initial stance period T1, a mid-stance period T2, a terminal-stance period T3, and a pre-swing period T4. The swing phase is further subdivided into an initial swing period T5, a mid-swing period T6, and a terminal swing period T7. FIG. 6 is an example and is not intended to limit the periods constituting one gait cycle, the names of these periods, or the like.

As illustrated in FIG. 6, a plurality of events (also referred to as gait events) occur in gait. P1 indicates an event (heel strike) in which the heel of the right foot touches the ground surface (HS: Heel Strike). P2 indicates an event (opposite toe off) in which the toe of the left foot is separated from the ground surface in a state in which the sole of the right foot is in contact with the ground surface (OTO: Opposite Toe Off). P3 indicates an event (heel rise) in which the heel of the right foot lifts in a state in which the sole of the right foot is in contact with the ground surface (HR: Heel Rise). P4 indicates an event (opposite heel strike) in which the heel of the left foot touches the ground surface (OHS: Opposite Heel Strike). P5 indicates an event (toe off) in which the toe of the right foot is separated from the ground surface in a state in which the sole of the left foot is in contact with the ground surface (TO: Toe Off). P6 indicates an event (foot adjacent) in which the left foot and the right foot cross each other in a state in which the sole of the left foot is in contact with the ground surface (FA: Foot Adjacent). P7 indicates an event (tibia vertical) in which the tibia of the right foot is approximately perpendicular to the ground surface in a state in which the sole of the left foot is in contact with the ground surface (TV: Tibia Vertical). P8 indicates an event (heel contact) in which the heel of the right foot touches the ground surface (HC: Heel Contact). P8 serves not only as the end point of the gait cycle starting from P1 but also the start point of the next gait cycle. FIG. 6 is an example and not intended to limit an event that occurs during gait or a name of an event.

Figure 7:
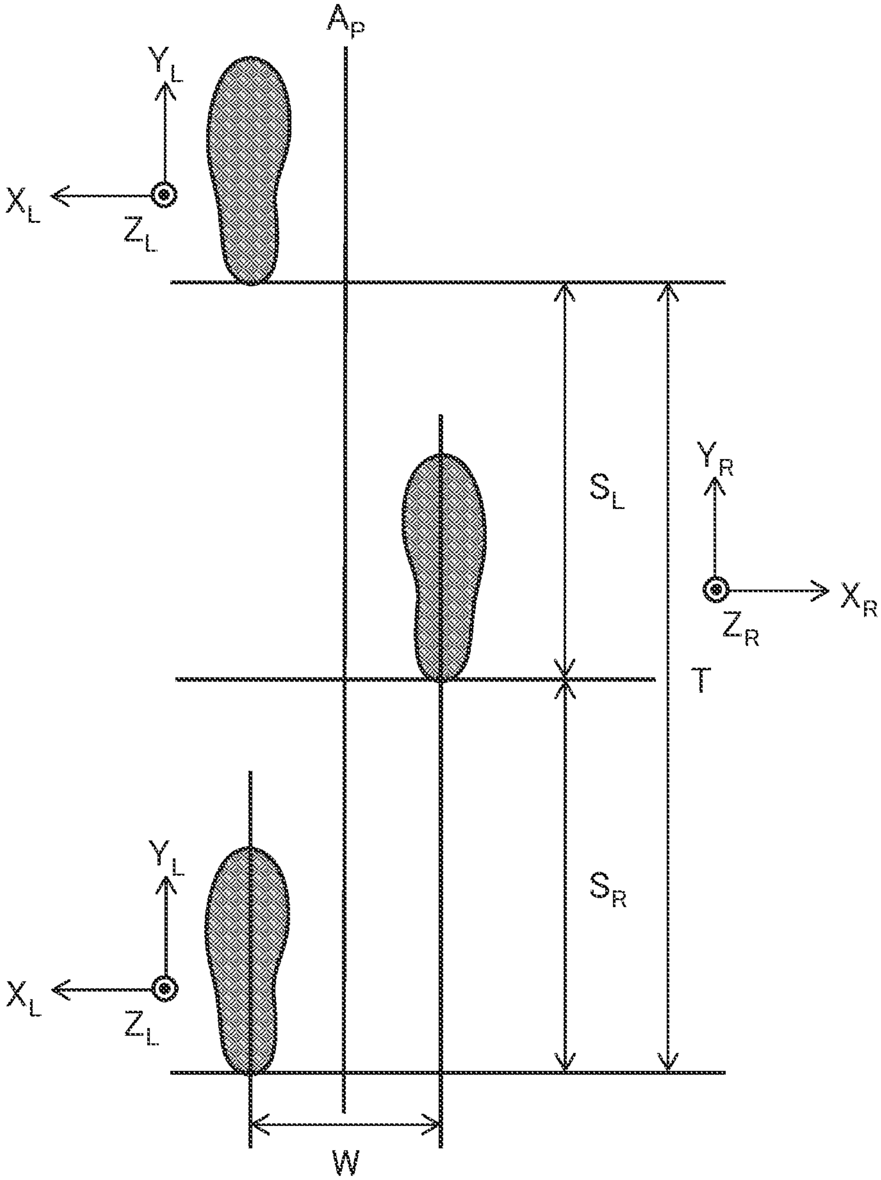
FIG. 7 is a conceptual diagram for explaining gait parameters related to a gait measurement system according to the present disclosure.

FIG. 7 is a conceptual diagram for explaining an example of gait parameters. FIG. 7 illustrates an example in which different coordinate systems are set for the left foot and the right foot. A right foot step length $S_R$, a left foot step length $S_L$, a stride length T, and a step width W are illustrated in FIG. 7. The right foot step length $S_R$ and the left foot step length $S_L$ are step lengths. A traveling axis $A_P$ that is parallel to an axis of the traveling direction (the Y-axis) and substantially equivalent to loci connecting middle points between the left and right feet is illustrated in FIG. 7. The right foot step length $S_R$ is a difference in the Y coordinate between the heel of the right foot and the heel of the left foot when the state in which the sole of the left foot is in contact with the ground surface transitions to the state in which the heel of the right foot swung out in the traveling direction lands. The left foot step length $S_L$ is a difference in the Y coordinate between the heel of the left foot and the heel of the right foot when the state in which the sole of the right foot is in contact with the ground surface transitions to the state in which the heel of the left foot swung out in the traveling direction lands. The stride length T is the sum of the right foot step length $S_R$ and the left foot step length $S_L$. The step width W is an interval between the right foot and the left foot. In FIG. 7, the step width W is a difference between the center line (the $X_R$ coordinate) of the heel of the right foot in the grounded state and the center line (the $X_L$ coordinate) of the heel of the left foot in the grounded state.

The communication unit 13 (communication means) receives the measurement start signal from the gait information generation device 15. The communication unit 13 outputs the received measurement start signal to the control unit 12. The communication unit 13 acquires the sensor data measured in response to the measurement start signal from the control unit 12. The communication unit 13 transmits the acquired sensor data to the gait information generation device 15. The communication unit 13 may be configured to transmit the sensor data at a preset transmission timing. For example, the communication unit 13 transmits the sensor data via wireless communication. The sensor data transmitted from the communication unit 13 is received by the gait information generation device 15. The transmission timing of the sensor data is not particularly limited. For example, the communication unit 13 transmits the sensor data in real time in response to the measurement of the sensor data. For example, the communication unit 13 may store the sensor data measured during a predetermined period and collectively transmit the stored sensor data at a preset timing.

For example, the communication unit 13 transmits the sensor data to the gait information generation device 15 via wireless communication. For example, the communication unit 13 transmits the sensor data to the gait information generation device 15 via a wireless communication function (not illustrated) conforming to a standard such as Bluetooth (registered trademark) or WiFi (registered trademark). The communication function of the communication unit 13 may conform to a standard other than Bluetooth (registered trademark) or WiFi (registered trademark). The communication unit 13 may transmit the sensor data to the gait information generation device 15 via a wire such as a cable.

Gait Information Generation Device

Figure 8:
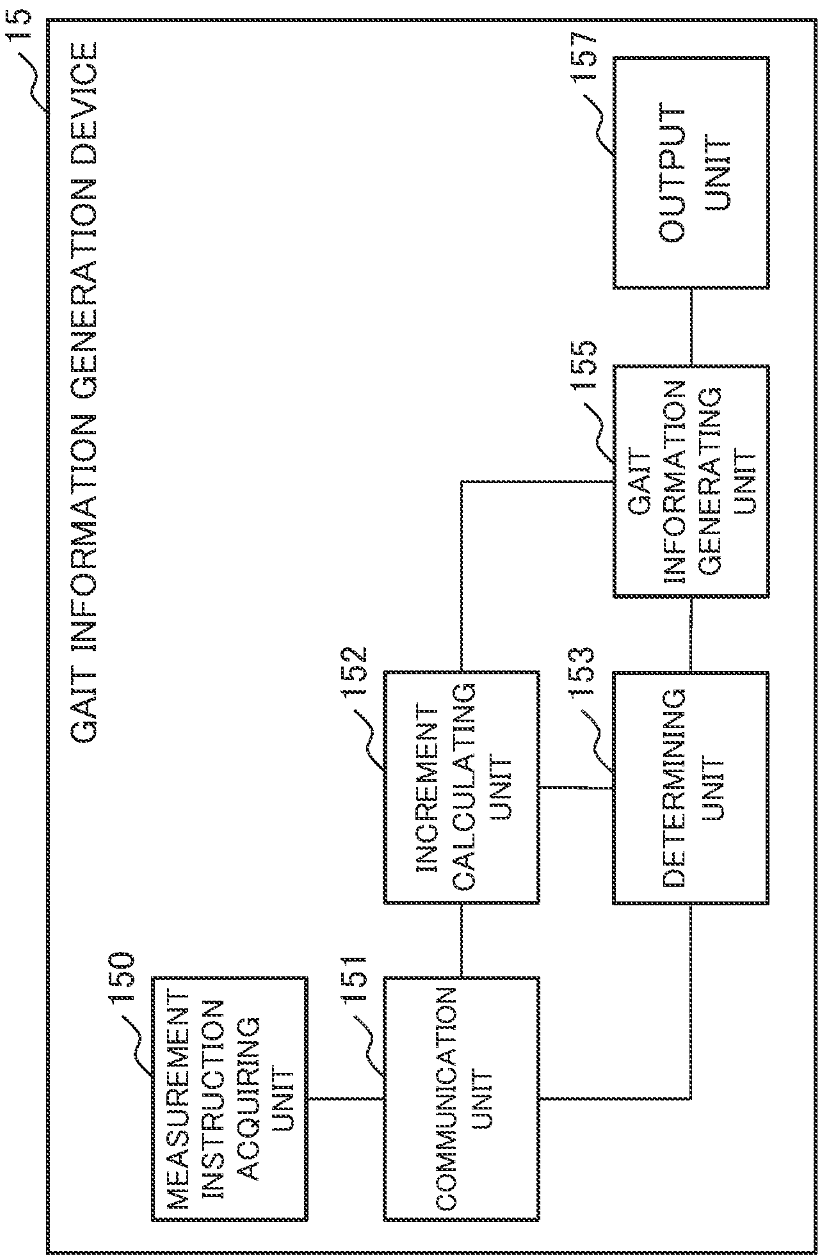
FIG. 8 is a block diagram illustrating an example of a configuration of a gait information generation device included in a gait measurement system according to the present disclosure.

FIG. 8 is a block diagram illustrating an example of a configuration of the gait information generation device 15. The gait information generation device 15 includes a measurement instruction acquiring unit 150, a communication unit 151, an increment calculating unit 152, a determining unit 153, a gait information generating unit 155, and an output unit 157.

The measurement instruction acquiring unit 150 (measurement instruction acquiring means) receives a measurement start instruction from the user. The measurement start instruction is input in response to an operation by the user. For example, an application (software) having the function of the gait information generation device 15 is installed in a mobile terminal (not illustrated) carried by the user. When the application is activated, a user interface for measuring the gait parameters including the step width is displayed on a screen of the mobile terminal carried by the user.

Figure 9:
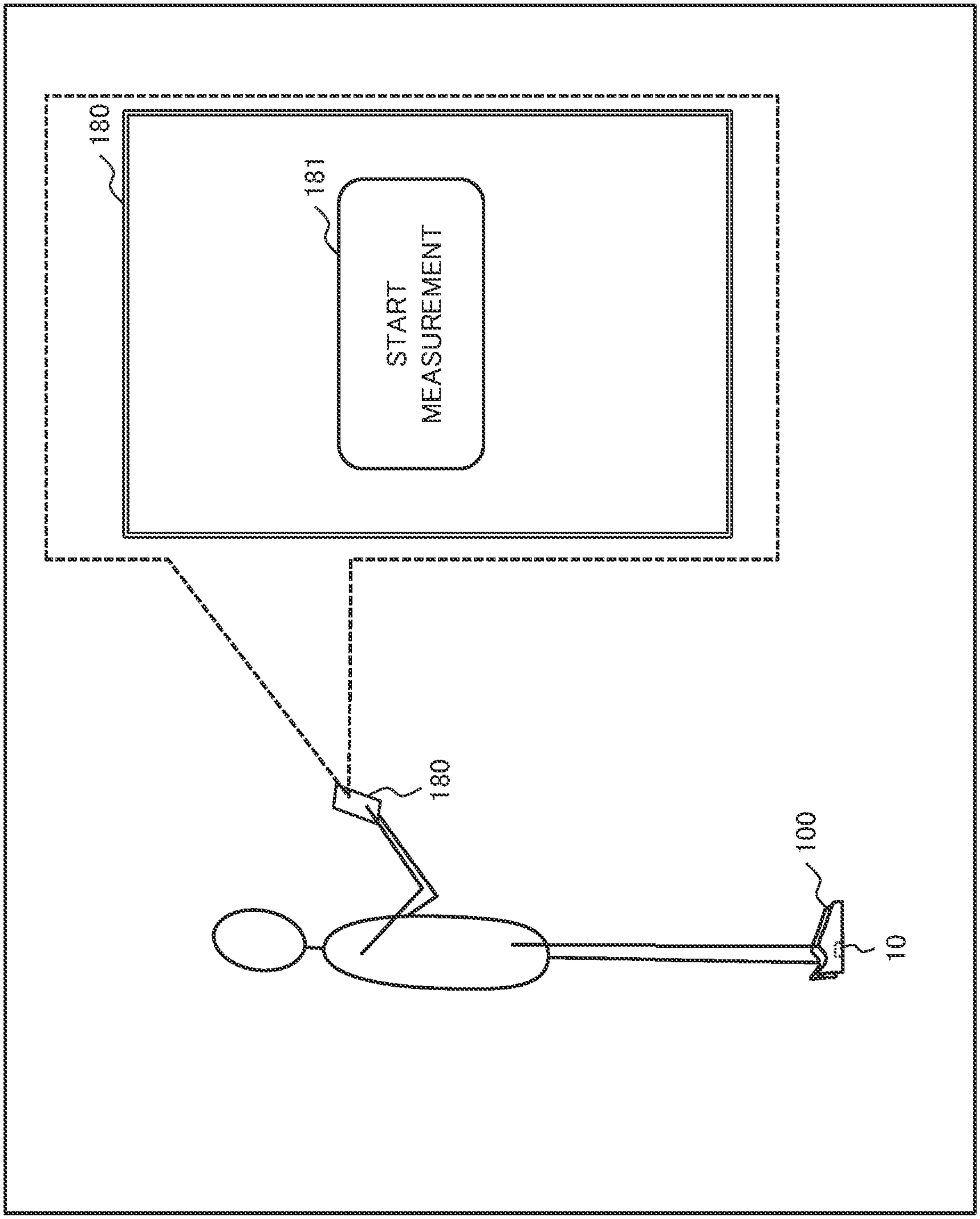
FIG. 9 is a conceptual diagram illustrating an example of a user interface displayed on a screen of a mobile terminal of a user who uses a gait measurement system according to the present disclosure.

FIG. 9 is a conceptual diagram illustrating an example of the user interface displayed on the screen of the mobile terminal 180 carried by the user. A measurement start button 181 is displayed on the user interface. The user stands by in a state in which the heels of both feet are aligned, and taps the measurement start button 181 displayed on the screen of the mobile terminal in accordance with a timing at which gait starts. The measurement instruction acquiring unit 150 outputs the measurement start signal to the communication unit 151 in response to the user tapping the measurement start button 181. For example, in response to the tap on the measurement start button 181, a voice instruction such as "Please stand with your heels aligned" may be output from the mobile terminal 180.

The communication unit 151 (communication means) acquires the measurement start signal from the measurement instruction acquiring unit 150. The communication unit 151 transmits the acquired measurement start signal to the sensor data measurement device 10. The communication unit 151 receives the sensor data measured in response to the measurement start signal from the sensor data measurement device 10. The communication unit 151 outputs the received sensor data to the increment calculating unit 152. The communication unit 151 acquires the measurement end signal from the determining unit 153. The communication unit 151 transmits the acquired measurement end signal to the sensor data measurement device 10.

For example, the communication unit 151 receives the sensor data via wireless communication. The sensor data received by the communication unit 151 is used for calculation of the gait parameters including the step width. For example, the communication unit 151 receives the sensor data transmitted from the sensor data measurement device 10 via wireless communication. For example, the communication unit 151 receives the sensor data from the sensor data measurement device 10 via a wireless communication function (not illustrated) conforming to a standard such as Bluetooth (registered trademark) or WiFi (registered trademark). The communication function of the communication unit 151 may conform to a standard other than Bluetooth (registered trademark) or WiFi (registered trademark). The communication unit 151 may be configured to receive the sensor data from the sensor data measurement device 10 via a wire such as a cable.

The increment calculating unit 152 (increment calculating means) acquires the sensor data from the communication unit 151. The increment calculating unit 152 acquires at least lateral acceleration of the sensor data. The increment calculating unit 152 performs second-order integral on the lateral acceleration and calculates an increment of a lateral distance. The increment calculating unit 152 separately calculates an increment of the lateral distance for each of the left foot and the right foot.

Figure 10:
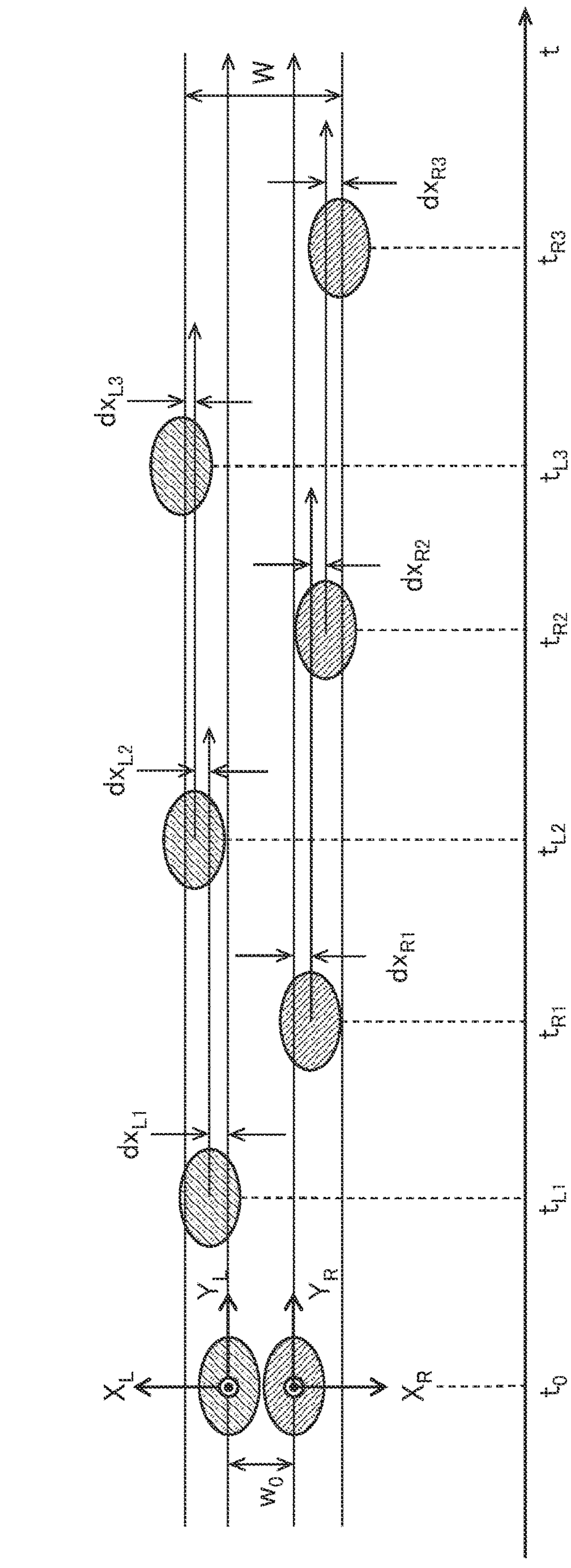
FIG. 10 is a conceptual diagram for explaining a step width measured by a gait measurement system according to the present disclosure.

FIG. 10 is a conceptual diagram for explaining calculation of the increment of the lateral distance by the increment calculating unit 152. FIG. 10 illustrates a position of the foot in a situation in which the user has walked a few steps from a state in which the user is upright with both feet aligned. In the example of FIG. 10, a first step is taken with the left foot. FIG. 10 illustrates a state in which time passes from left to right. At a timing $t_0$, the user is standing upright with both feet aligned. A distance between the heel center lines (heel center distance) of both feet at a timing $t_0$ (initial state) is $w_0$. The heel center distance $w_0$ in the initial state may be measured in advance and registered in a storage unit (not illustrated) of the gait information generation device 15. The size of the footwear on which the sensor data measurement device 10 is mounted is constant as long as the outer shape of the footwear is not changed. Therefore, the heel center distance $w_0$ may be set in response to the input of a type or size of the footwear.

In response to the measurement start signal transmitted in response to the user tapping the measurement start button 181, the measurement of the gait parameters (step width) by the sensor data measurement device 10 starts. A timing $t_{L1}$ indicates a state in which the sole of the foot touches the ground surface at the first step of the left foot. An increment in the left direction by transition from the timing $t_0$ to the timing $t_{L1}$ is $dx_{L1}$. A timing $t_{R1}$ indicates a state in which the sole of the foot touches the ground surface at the first step of the right foot. An increment in the right direction by transition from the timing $t_0$ to the timing $t_{R1}$ is $dx_{R1}$. A timing $t_{L2}$ indicates a state in which the sole of the foot touches the ground surface at the second step of the left foot. An increment in the left direction by transition from the timing $t_{L1}$ to the timing $t_{L2}$ is $dx_{L2}$. A timing $t_{R2}$ indicates a state in which the sole of the foot touches the ground surface at the second step of the right foot. An increment in the right direction by transition from the timing $t_{R1}$ to the timing $t_{R2}$ is $dx_{R2}$. A timing $t_{L3}$ indicates a state in which the sole of the foot touches the ground surface at the third step of the left foot. An increment in the left direction by transition from the timing $t_{L2}$ to the timing $t_{L3}$ is $dx_{L3}$. A timing $t_{R3}$ indicates a state in which the sole of the foot touches the ground surface at the third step of the right foot. An increment in the right direction by transition from the timing $t_{R2}$ to the timing $t_{R3}$ is $dx_{R3}$.

The determining unit 153 (determining means) acquires the increment of the lateral distance according to gait. The determining unit 153 determines the end of the measurement in response to the acquired value of the increment of the lateral distance. The increment of the lateral distance approaches 0 as the number of steps increases. For example, when the value of the increment becomes smaller than a preset reference measurement end value, the determining unit 153 determines that the measurement is ended. For example, when a change in the increment becomes smaller than a change value serving as the preset measurement end reference, the determining unit 153 determines that the measurement is ended. Typically, it is possible to calculate the step width when sensor data of three to five steps are acquired. Therefore, the determining unit 153 may be configured to determine that the measurement is ended in response to the preset number of steps.

When it is determined that the measurement is ended, the determining unit 153 outputs a calculation instruction signal for giving an instruction to calculate the gait parameters including the step width to the gait information generating unit 155. When it is determined that the measurement is ended, the determining unit 153 outputs the measurement end signal to the communication unit 151.

The gait information generating unit 155 (step width calculating means) acquires the calculation instruction signal from the determining unit 153. In response to the acquisition of the calculation instruction signal, the gait information generating unit 155 acquires an increment in a measurement period of time from the measurement start to the measurement end from the increment calculating unit 152. The gait information generating unit 155 acquires the heel center distance $w_0$ in the initial state.

The gait information generating unit 155 acquires the heel center distance $w_0$ at the timing $t_0$ (initial state) and the increment according to gait. The gait information generating unit 155 calculates the sum of the heel center distance $w_0$ and the sum total of the increments. The sum of the heel center distance $w_0$ and the sum total of the increments is substantially equivalent to the step width W. The gait information generating unit 155 calculates the step width W by using the following Formula 1.

[Math. 1]

$$W = w_0 + \sum_{i=1}^{n}(dx_{Li} + dx_{Ri}) \quad (1)$$

In Formula 1 described above, n indicates the number of steps from the start of the measurement to the end of the measurement (n is a natural number). For example, n is set to 3 to 5. $dx_{Li}$ indicates the increment of the heel center distance at an i-th step of the left foot (i is a natural number). $dx_{Ri}$ indicates the increment of the heel center distance at an i-th step of the right foot. In practical use, influence of drift or rotation is included in the sensor data. Therefore, drift correction or rotation correction may be performed on the value of the calculated step width.

The gait information generating unit 155 generates information (gait information) related to the gait based on the calculated step width W. For example, the gait information generating unit 155 generates the gait information including the value of the calculated step width W. The gait information generating unit 155 outputs the generated gait information to the output unit 157. The gait information generated by the gait information generating unit 155 is not particularly limited as long as the information is related to the step width.

In ideal gait, the step width may be relatively narrow. An appropriate value of the step width in the ideal gait is a value within a range of 5 to 13 centimeters (cm). Therefore, the gait information generating unit 155 may generate the gait information according to a difference from the appropriate value of the step width. For example, in a case in which the step width is within a range of 5 to 13 centimeters (cm), the gait information generating unit 155 generates the gait information with a text such as “Your step width is ideal”. For example, in a case in which the step width is out of the range of 5 to 13 centimeters (cm), the gait information generating unit 155 generates the gait information with a text of “Be aware of taking smaller step widths”. The appropriate value of the step width depends on attribute data such as an age, a height, and a leg length. Therefore, the appropriate value of the step width may be decided based on the attribute data of the user.

Examples of factors contributing to an increased step width include an unstable feeling, a fear, and a stiff chest. For example, in a case in which the step width is out of the range of 5 to 13 centimeters (cm), the gait information generating unit 155 may generate the gait information indicating the factor such as an unstable feeling, a fear, or a stiff chest.

The output unit 157 (output means) acquires the gait information from the gait information generating unit 155. The output unit 157 outputs the acquired gait information. For example, the output unit 157 causes the gait information to be displayed on the screen of the mobile terminal 180 of the subject (the user). For example, the output unit 157 outputs the gait information to an external system or the like that uses the gait information. The use of the gait information output from the output unit 157 is not particularly limited.

First Application Example

Figure 11:
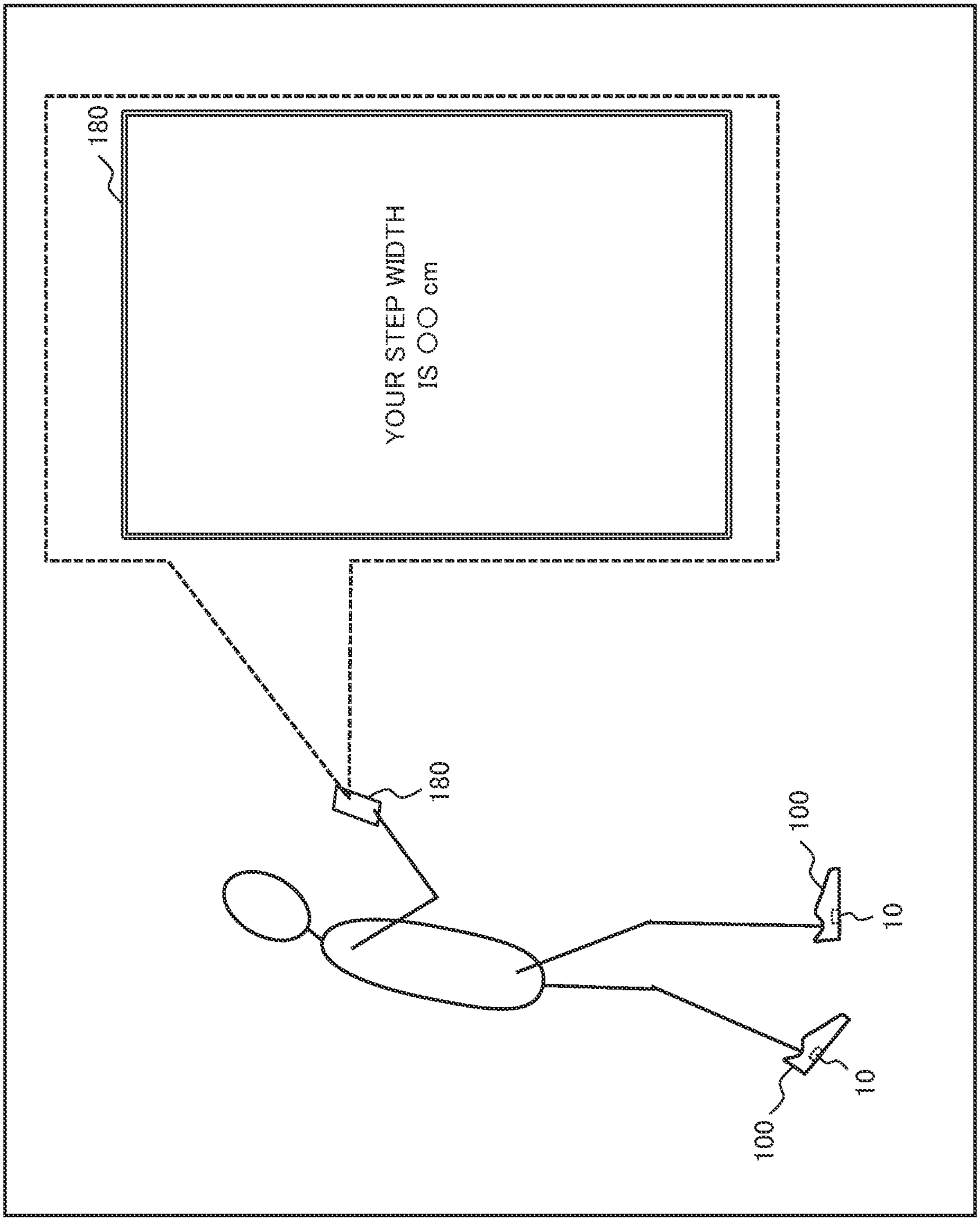
FIG. 11 is a conceptual diagram for explaining a first application example according to the present disclosure.

FIG. 11 is a conceptual diagram illustrating an example (first application example) in which the gait information related to the step width output from the gait information generation device 15 is displayed on the screen of the mobile terminal 180 carried by the user during gait while wearing the shoe 100 in which the sensor data measurement device 10 is mounted. FIG. 11 is an example in which the gait information based on the sensor data measured in response to the user’s gait is displayed on the screen of the mobile terminal 180. In the example of FIG. 11, the gait information related to the step width such as “Your step width is ○○ cm” is displayed on the screen of the mobile terminal 180. The user who has checked the gait information displayed on the display unit of the mobile terminal 180 can recognize information related to his/her own step width.

For example, the gait information generation device 15 is connected to an external system or the like built in a cloud or a server via the mobile terminal 180 carried by the subject (user). The mobile terminal 180 is a portable communication device. For example, the mobile terminal 180 is a portable communication device having a communication function, such as a smartphone, a smart watch, or a mobile phone. For example, the gait information generation device 15 is connected to the mobile terminal 180 via a wire such as a cable. For example, the gait information generation device 15 is connected to the mobile terminal 180 via wireless communication. For example, the gait information generation device 15 is connected to the mobile terminal 180 via a wireless communication function (not illustrated) conforming to a standard such as Bluetooth (registered trademark) or WiFi (registered trademark). The communication function of the gait information generation device 15 may conform to a standard other than Bluetooth (registered trademark) or WiFi (registered trademark). The information related to the step width may be used by another application installed in the mobile terminal 180. In that case, the mobile terminal 180 executes a process that uses the information related to the step width by application software or the like installed in the mobile terminal 180.

Operation

Next, an operation of the gait measurement system 1 according to the present example embodiment will be described with reference to the drawings. Hereinafter, the sensor data measurement device 10 and the gait information generation device 15 included in the gait measurement system 1 will be individually described.

Sensor Data Measurement Device

Figure 12:
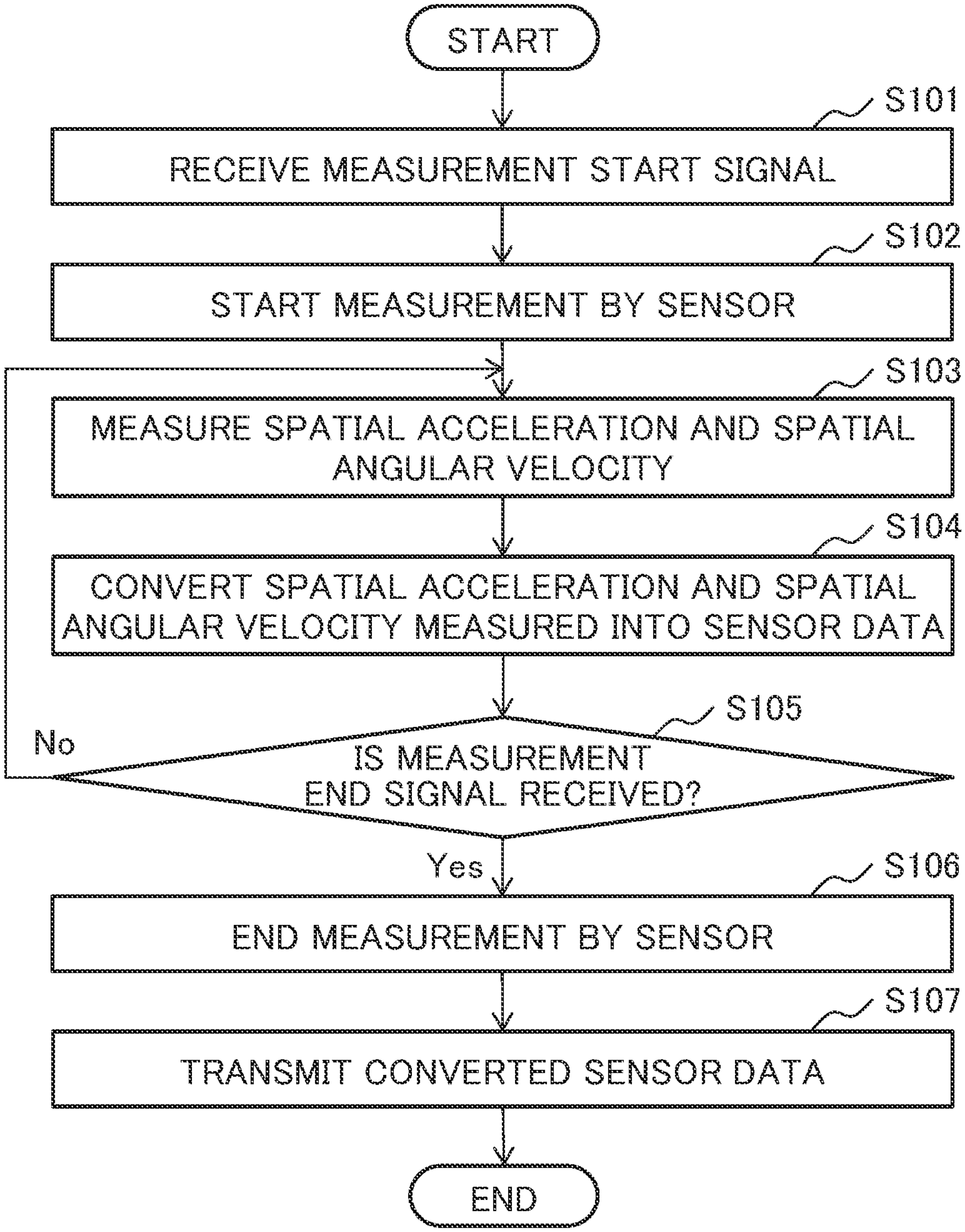
FIG. 12 is a flowchart for explaining an operation of a sensor data measurement device included in a gait measurement system according to the present disclosure.

FIG. 12 is a flowchart for explaining an example of an operation of the sensor data measurement device 10. In the description based on the flowchart of FIG. 12, components included in the sensor data measurement device 10 will be described as main operation entities. A main operation entity of a process according to the flowchart of FIG. 12 may be the sensor data measurement device 10.

In FIG. 12, first, the communication unit 13 receives the measurement start signal from the gait information generation device 15 (step S101).

Next, the control unit 12 causes the sensor 11 to start measurement (step S102).

Next, the sensor 11 measures spatial acceleration and spatial angular velocity (step S103).

Next, the control unit 12 converts the spatial acceleration and the spatial angular velocity measured by the sensor 11 into sensor data (step S104).

Here, when the communication unit 13 receives the measurement end signal (Yes in step S105), the control unit 12 causes the sensor 11 to end the measurement (step S106). When the communication unit 13 has not received the measurement end signal (No in step S105), the process returns to step S103.

After step S106, the communication unit 13 transmits the converted sensor data to the gait information generation device 15 (step S107). The sensor data transmitted to the gait information generation device 15 is used for calculation of the gait parameters including the step width.

Gait Information Generation Device

Figure 13:
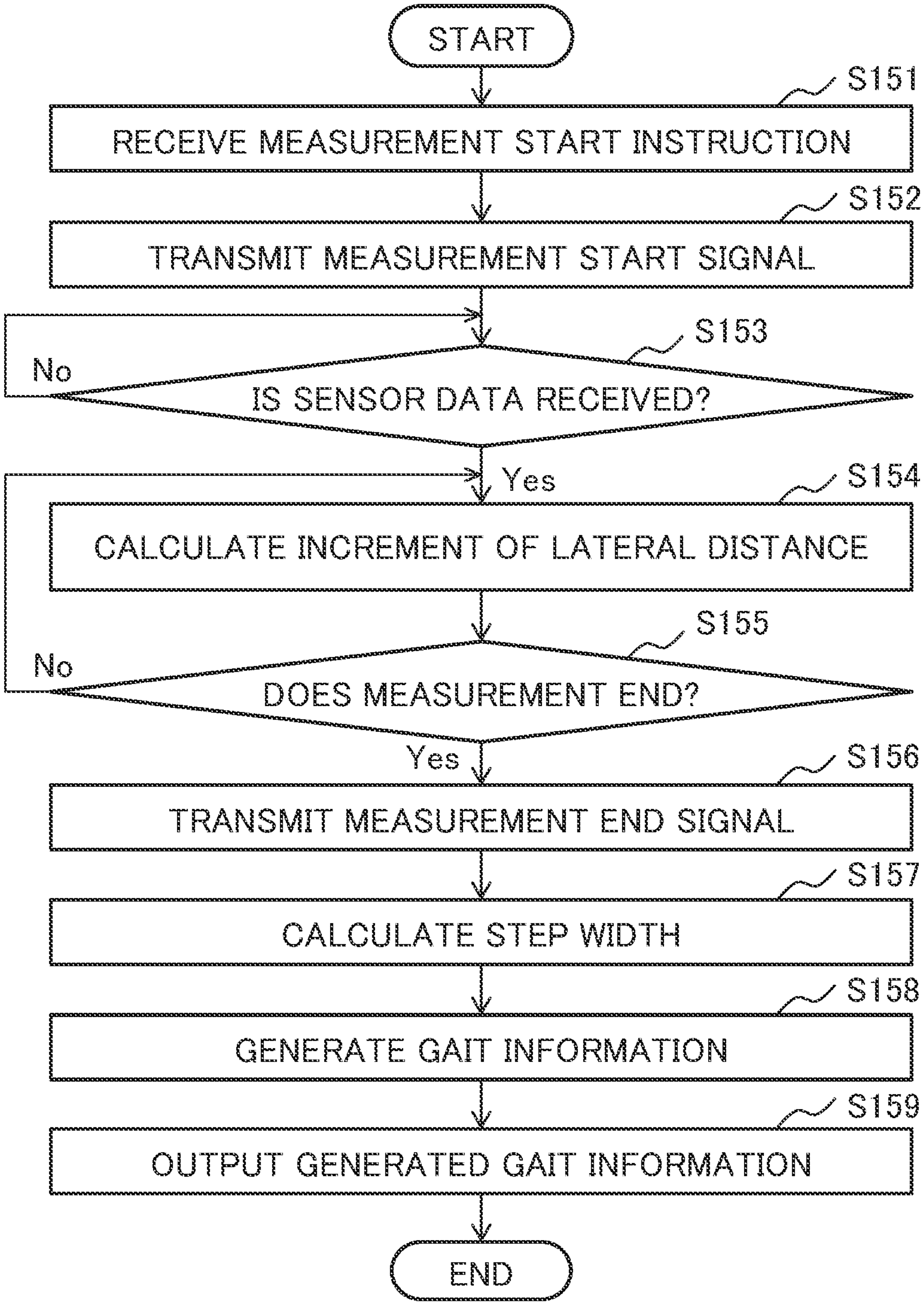
FIG. 13 is a flowchart for explaining an operation of a gait information generation device included in a gait measurement system according to the present disclosure.

FIG. 13 is a flowchart for explaining an example of an operation of the gait information generation device 15. In the description based on the flowchart of FIG. 13, components of the gait information generation device 15 will be described as main operation entities. A main operation entity of a process according to the flowchart of FIG. 13 may be the gait information generation device 15.

In FIG. 13, first, the measurement instruction acquiring unit 150 receives the measurement start instruction input by the user (step S151).

Next, the communication unit 151 transmits the measurement start signal to the sensor data measurement device 10 (step S152).

Next, when the communication unit 151 receives the sensor data (Yes in step S153), the increment calculating unit 152 calculates the increment of the lateral distance (step S154). When the communication unit 151 has not received the sensor data (No in step S153), the process is on standby until the sensor data is received.

After step S154, the determining unit 153 determines whether the measurement is ended (step S155). When the determining unit 153 determines that the measurement is ended (Yes in step S155), the communication unit 151 transmits the measurement end signal to the sensor data measurement device 10 (step S156). When the determining unit 153 determines that the measurement is not ended (No in step S155), the process of step S154 is continued.

After step S156, the gait information generating unit 155 calculates the step width (step S157).

Next, the gait information generating unit 155 generates the gait information related to the step width (step S158).

Next, the output unit 157 outputs the gait information related to the calculated step width (step S159). For example, the gait information related to the step width is output to the mobile terminal 180 carried by the user. For example, the gait information related to the step width is displayed on the screen of the mobile terminal 180. For example, the gait information related to the step width is output to a system that executes a process that uses the gait information.

As described above, the gait measurement system of the present example embodiment includes the sensor data measurement device and the gait information generation device. The sensor data measurement device is installed on the user's footwear. The sensor data measurement device includes the sensor including the acceleration sensor that measures the accelerations in three axial directions and the angular velocity sensor that measures the angular velocities around the three axes. The sensor data measurement device outputs the sensor data based on the physical quantities measured by the acceleration sensor and the angular velocity sensor to the gait information generation device.

The gait information generation device includes the communication unit, the increment calculating unit, the determining unit, the gait information generating unit, and the output unit. The communication unit acquires the sensor data measured in response to the motion of the foot. The increment calculating unit calculates the increment of the lateral distance using the lateral acceleration included in the sensor data. The determining unit determines the measurement end of the sensor data in response to the increment of the lateral distance. When it is determined that the measurement is ended in response to the increment of the lateral distance, the determining unit outputs the calculation instruction signal for giving an instruction to calculate the gait parameters including the step width. The gait information generating unit executes the calculation of the gait parameters including the step width in response to the calculation instruction signal. The gait information generating unit calculates, as the step width, the sum of the heel center distance substantially equivalent to the distance between the center lines of the heels of both feet in the initial state and the sum total of the increments of the lateral distance. The gait information generating unit generates the gait information related to the calculated step width. The output unit outputs the generated gait information.

The gait information generation device of the present example embodiment determines the measurement end in response to the increment of the lateral distance, and executes the calculation of the gait parameters including the step width. The gait information generation device of the present example embodiment generates the gait information related to the step width by using the lateral acceleration included in the sensor data measured in response to the motion of the foot. According to the technique of the present example embodiment, it is possible to generate the gait information related to the step width as long as it is possible to acquire the sensor data measured by the sensor installed in the footwear. That is, according to the present example embodiment, it is possible to generate the gait information related to the step width with a simple configuration.

In one aspect of the present example embodiment, the increment calculating unit calculates the lateral distance by the second-order integral of the lateral acceleration. The increment calculating unit calculates the difference between the lateral distances of both feet as the increment of the lateral distance. According to the present aspect, the step width can be calculated using the increment of the lateral distance calculated by the second-order integral of the lateral acceleration.

In one aspect of the present example embodiment, the increment calculating unit calculates the difference of the lateral distance for each step of both feet as the increment of the lateral distance. Therefore, according to the present aspect, the step width can be calculated using the increment of the lateral distance for each step of both feet.

In one aspect of the present example embodiment, the determining unit determines that the measurement is ended when the increment of the lateral distance becomes smaller than the preset reference measurement end value. According to the present aspect, the measurement end can be determined based on a clear relationship between the reference measurement end value and the lateral distance.

Second Example Embodiment

Next, a gait measurement system according to a second example embodiment will be described with reference to the drawings. The gait measurement system of the present example embodiment calculates a step length in addition to the step width. The gait measurement system of the present example embodiment outputs the gait information related to the calculated step width and the step length.

Configuration

Figure 14:
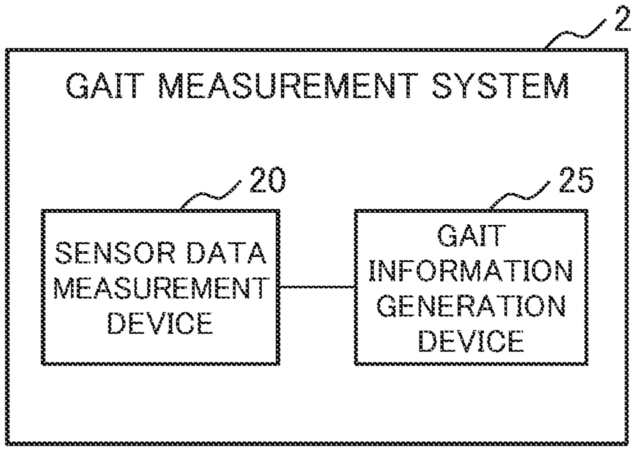
FIG. 14 is a block diagram illustrating an example of a configuration of a gait measurement system according to the present disclosure.

FIG. 14 is a block diagram illustrating an example of a configuration of the gait measurement system 2 according to the present example embodiment. The gait measurement system 2 includes a sensor data measurement device 20 and a gait information generation device 25. The sensor data measurement device 20 has a configuration similar to the sensor data measurement device 10 of the first example embodiment. The sensor data measurement device 20 is installed on footwear or the like of the subject (user) who is a measurement target for the gait parameters including the step width and the step length. For example, functions of the gait information generation device 25 are installed in a mobile terminal carried by the subject. The functions of the gait information generation device 25 may be implemented in a server or a cloud connected to a mobile terminal carried by the subject via a communication network. Hereinafter, description of the sensor data measurement device 20 will be omitted, and a configuration of the gait information generation device 25 will be described.

Gait Information Generation Device

Figure 15:
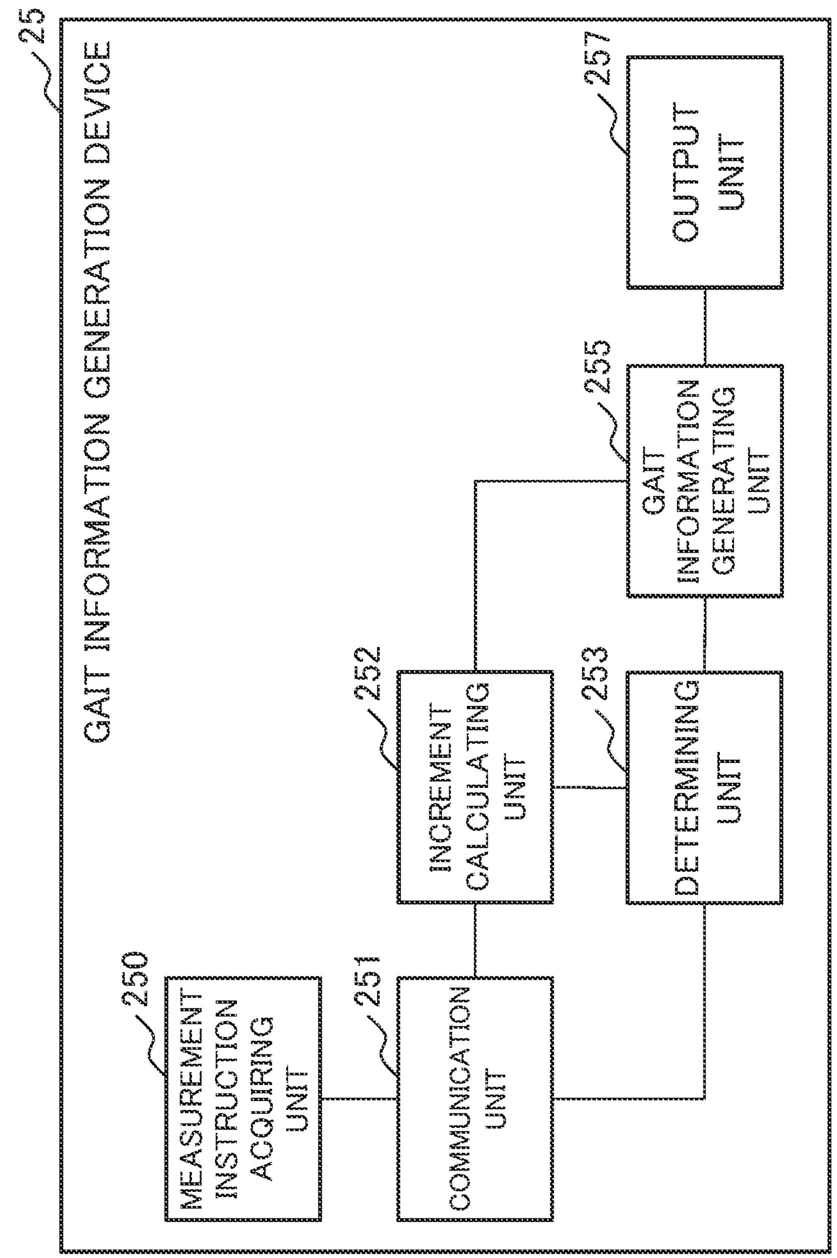
FIG. 15 is a block diagram illustrating an example of a configuration of a sensor data measurement device included in a gait measurement system according to the present disclosure.

FIG. 15 is a block diagram illustrating an example of a configuration of the gait information generation device 25. The gait information generation device 25 includes a measurement instruction acquiring unit 250, a communication unit 251, an increment calculating unit 252, a determining unit 253, a gait information generating unit 255, and an output unit 257.

The measurement instruction acquiring unit 250 (measurement instruction acquiring means) has a configuration similar to the measurement instruction acquiring unit 150 of the first example embodiment. The measurement instruction acquiring unit 250 receives the measurement start instruction from the user. The measurement start instruction is input in response to an operation by the user.

The communication unit 251 (communication means) has a configuration similar to the communication unit 251 of the first example embodiment. The communication unit 251 acquires the measurement start signal from the measurement instruction acquiring unit 250. The communication unit 251 transmits the acquired measurement start signal to the sensor data measurement device 20. The communication unit 251 receives the sensor data measured in response to the measurement start signal from the sensor data measurement device 20. The communication unit 251 outputs the received sensor data to the increment calculating unit 252. The communication unit 251 acquires the measurement end signal from the determining unit 253. The communication unit 251 transmits the acquired measurement end signal to the sensor data measurement device 20.

The increment calculating unit 252 (increment calculating means) has a configuration similar to the increment calculating unit 152 of the first example embodiment. The increment calculating unit 252 acquires the sensor data from the communication unit 251. The increment calculating unit 252 acquires at least lateral acceleration of the sensor data. The increment calculating unit 252 performs second-order integral on the lateral acceleration and calculates an increment of the lateral distance. The increment calculating unit 252 separately calculates an increment for each of the left foot and the right foot.

The determining unit 253 (determining means) has a configuration similar to the determining unit 153 of the first example embodiment. The determining unit 253 acquires an increment according to gait. The determining unit 253 determines the end of the measurement in response to a value of the acquired increment. For example, when the value of the increment reaches a preset reference measurement end value, the determining unit 253 determines that the measurement is ended. For example, when a change in the increment becomes smaller than a change value serving as the preset measurement end reference, the determining unit 253 determines that the measurement is ended. When it is determined that the measurement is ended, the determining unit 253 outputs the calculation instruction signal to the gait information generating unit 255. When it is determined that the measurement is ended, the determining unit 253 outputs the measurement end signal to the communication unit 251.

The gait information generating unit 255 (step width calculating means) acquires the calculation instruction signal from the determining unit 253. In response to the acquisition of the calculation instruction signal, the gait information generating unit 255 acquires an increment in a measurement period of time from the measurement start to the measurement end from the increment calculating unit 252. The gait information generating unit 255 acquires the heel center distance $w_0$ in the initial state.

The gait information generating unit 255 acquires the heel center distance $w_0$ at the timing $t_0$ (initial state) and the increment according to gait. The gait information generating unit 255 calculates the sum of the heel center distance $w_0$ and the sum total of the increments of the distance. The sum of the heel center distance $w_0$ and the sum total of the increments of the distance is substantially equivalent to the step width.

The gait information generating unit 255 acquires the sensor data used for calculating the step length in response to the acquisition of the calculation instruction signal. For example, the gait information generating unit 255 acquires the sensor data from the communication unit 251. The gait information generating unit 255 may be configured to acquire the sensor data stored in a buffer (not illustrated). The gait information generating unit 255 calculates the step length using the acquired sensor data. A method of calculating the step length by the gait information generating unit 255 is not particularly limited.

For example, the gait information generating unit 255 acquires time-series data of the acceleration in the traveling direction related to the right foot. The gait information generating unit 255 performs second-order integral on the acquired time-series data of the acceleration in the traveling direction, and generates time-series data of the loci in the traveling direction. The gait information generating unit 255 extracts a section between the toe off and the heel strike as a gait waveform of the loci in the traveling direction in one step from a gait waveform of the loci in the traveling direction in one gait cycle. The gait information generating unit 255 calculates an absolute value of a difference between a spatial position at the foot adjacent and a spatial position at the toe off by using the gait waveform of the loci in the traveling direction in one step. The absolute value of the difference between the spatial position at the foot adjacent and the spatial position at the toe off is substantially equivalent to a left foot step length $S_L$ (also referred to as a left foot step length) in a state in which the left foot is in the front and the right foot is behind. The gait information generating unit 255 calculates an absolute value of a difference between a spatial position at the timing of the foot adjacent and a spatial position at the heel strike by using the gait waveform of the loci in the traveling direction in one step. The absolute value of the difference between the spatial position at the timing of the foot adjacent and the spatial position at the heel strike is substantially equivalent to a right foot step length $S_R$ (also referred to as a right foot step length) in a state in which the right foot is in front and the left foot is behind.

For example, the gait information generating unit 255 calculates, as the step length, an average value of the left foot step length and the right foot step length of a few steps. The gait information generating unit 255 may calculate, as the step length of each foot, an average value of each of the left foot step length and the right foot step length of a few steps. The gait information generating unit 255 may calculate the step length by using the time-series data of the acceleration in the traveling direction related to the left foot. The gait information generating unit 255 may calculate the step length by using the time-series data of the acceleration in the traveling direction related to the right foot.

The gait information generating unit 255 generates information (gait information) related to the gait based on the calculated step width and the step length. For example, the gait information generating unit 255 generates the gait information including the value of the calculated step width and the step length. The gait information generating unit 255 outputs the generated gait information to the output unit 257. The gait information generated by the gait information generating unit 255 is not particularly limited as long as the information is related to at least one of the step width and the step length.

In ideal gait, the step length may be relatively wide, and the step width may be relatively narrow. The appropriate value of the step length in the ideal gait is a value obtained by multiplying the height by 0.45. For the elderly, the appropriate value of the step length in ideal gait is a value obtained by multiplying the height by 0.4. The appropriate value of the step width in the ideal gait is a value within a range of 5 to 13 centimeters (cm). Therefore, the gait information generating unit 255 may generate the gait information according to a difference from the appropriate values of the step length and the step width in the ideal gait.

For example, in a case in which the step width is within a range of 5 to 13 centimeters (cm), the gait information generating unit 255 generates the gait information with a text such as "Your step width is ideal". For example, in a case in which the step width is out of the range of 5 to 13 centimeters (cm), the gait information generating unit 255 generates the gait information with a text of "Be aware of taking smaller step widths".

Examples of factors contributing to an increased step width include an unstable feeling, a fear, and a stiff chest. For example, in a case in which the step width is out of the range of 5 to 13 centimeters (cm), the gait information generating unit 255 may generate the gait information related to an unstable feeling, a fear, a stiff chest, or the like. For example, in a case in which the step width is out of the range of 5 to 13 centimeters (cm), the gait information generating unit 255 may generate the gait information with a text "Let's relax".

For example, in a case in which the step length is close to the value obtained by multiplying the height by 0.45 (for example, within a range of 0.45±0.05), the gait information generating unit 255 generates the gait information with a text "Your step length is ideal". For example, in a case in which the step length significantly deviates from the value obtained by multiplying the height by 0.45 (for example, out of the range of 0.45±0.05), the gait information generating unit 255 generates the gait information with a text "Be aware of taking larger step length".

Examples of factors contributing to a narrowed step length include restrictions in the movable range of the lower limbs, restrictions in lumbar lordosis, and restrictions in thoracic rotation. Specifically, examples of factors contributing to restrictions in the movable range of the lower limbs include restrictions in hip extension, knee extension, ankle dorsiflexion, and toe metacarpo phalangeal (MP) joint extension. For example, in a case in which the step length significantly deviates from the value obtained by multiplying the height by 0.45, the gait information generating unit 255 may generate the gait information related to restrictions in the movable range of the lower limbs, restrictions in lumbar lordosis, and restrictions in thoracic rotation. For example, in a case in which the step length significantly deviates from the value obtained by multiplying the height by 0.45, the gait information generating unit 255 may generate the gait information with a text "Let's engage in exercises such as bending and stretching, forward bending, and body stretching".

The gait information generating unit 255 may generate a score (gait score) related to gait based on the gait parameters including the step width or the gait as the gait information. For example, the gait information generating unit 255 generates the gait score based on to the value of the step width or the step length. For example, the gait information generating unit 255 generates the gait score based on to the value of the step width and the step length. A method of deciding the gait score is not particularly limited.

The gait information generating unit 255 may generate information by machine learning. For example, the idealness of a calculated gait may be estimated by learning of gait data or a condition of a pedestrian obtained in the past and used as the gait information.

The output unit 257 (output means) acquires the gait information from the gait information generating unit 255. The output unit 257 outputs the acquired gait information. For example, the output unit 257 causes the gait information to be displayed on the screen of the mobile terminal of the subject (the user). For example, the output unit 257 outputs the gait information to an external system or the like that uses the gait information. The use of the gait information output from the output unit 257 is not particularly limited.

Second Application Example

Figure 16:
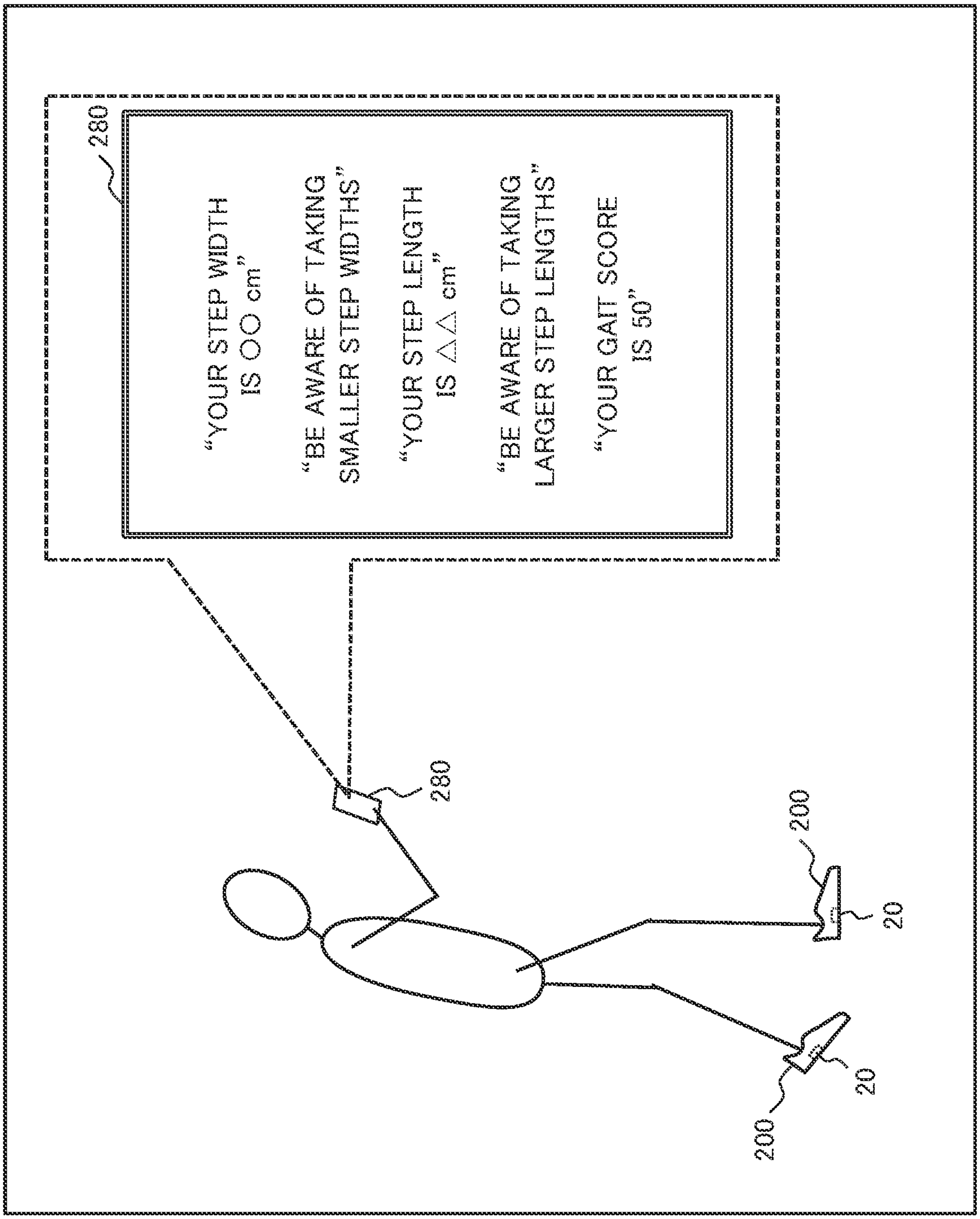
FIG. 16 is a conceptual diagram for explaining a second application example according to the present disclosure.

FIG. 16 is a conceptual diagram illustrating an example (second application example) in which the gait information related to the step width and the step length output from the gait information generation device 25 is displayed on the screen of the mobile terminal 280 carried by the user during gait while wearing the shoes 200 in which the sensor data measurement device 20 is mounted. FIG. 16 is an example in which the gait information related to the step width and the step length based on the sensor data measured in response to the user's gait is displayed on the screen of the mobile terminal 280.

In the example of FIG. 16, the gait information related to the step width such as "Your step width is ○○ cm" is displayed on the screen of the mobile terminal 280. In the example of FIG. 16, the gait information related to the step width such as "Be aware of taking smaller step widths" is displayed on the screen of the mobile terminal 280 in accordance with the value of the step width. In the example of FIG. 16, the gait information related to the step length such as "Your step length is ○○ cm" is displayed on the screen of the mobile terminal 280. In the example of FIG. 16, the gait information related to the step length such as "Be aware of taking smaller step lengths" is displayed on the screen of the mobile terminal 280 in accordance with the value of the step length. In the example of FIG. 16, a gait score according to the step width and the step length such as "Your gait score is 50" is displayed on the screen of the mobile terminal 280. The user who has checked the gait information displayed on the display unit of the mobile terminal 280 can recognize information related to his/her own step width and step length.

For example, the gait information generation device 25 is connected to an external system or the like built in a cloud or a server via the mobile terminal 280 carried by the subject (user). The mobile terminal 280 is a portable communication device. For example, the mobile terminal 280 is a portable communication device having a communication function, such as a smartphone, a smart watch, or a mobile phone. For example, the gait information generation device 25 is connected to the mobile terminal 280 via a wire such as a cable. For example, the gait information generation device 25 is connected to the mobile terminal 280 via wireless communication. For example, the gait information generation device 25 is connected to the mobile terminal 280 via a wireless communication function (not illustrated) conforming to a standard such as Bluetooth (registered trademark) or WiFi (registered trademark). The communication function of the gait information generation device 25 may conform to a standard other than Bluetooth (registered trademark) or WiFi (registered trademark). The information related to the step width may be used by another application installed in the mobile terminal 280. In that case, the mobile terminal 280 executes a process that uses the information related to the step width by application software or the like installed in the mobile terminal 280.

Third Application Example

Figure 17:
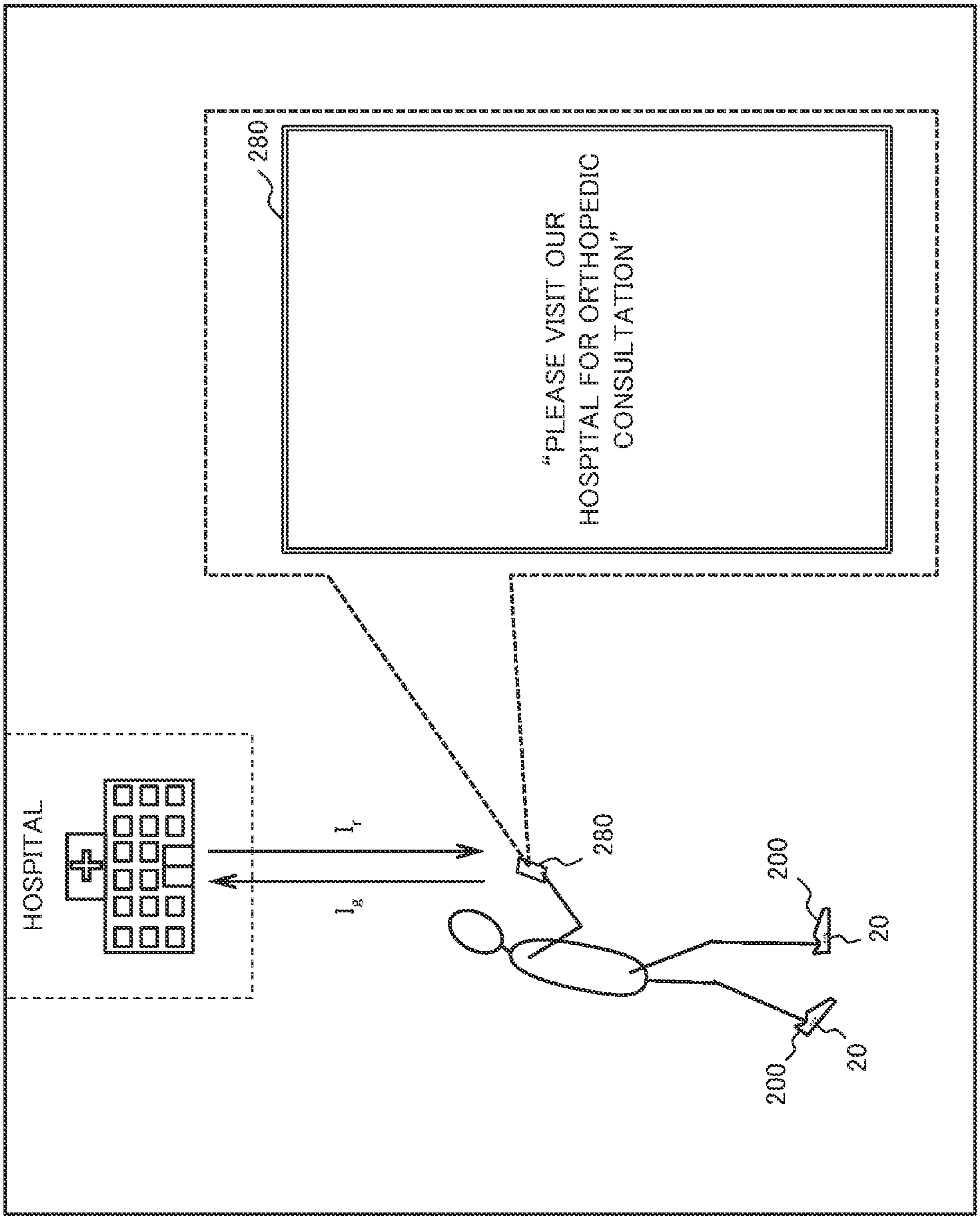
FIG. 17 is a conceptual diagram for explaining a third application example according to the present disclosure.

FIG. 17 is a conceptual diagram illustrating an example (third application example) in which action recommendation information from a doctor of a hospital which the user visits is displayed on the screen of the mobile terminal 280 carried by the user during gait while wearing the shoes 200 on which the sensor data measurement device 20 is mounted.

In the example of FIG. 17, gait information $I_g$ related to the step width and the step length based on the sensor data measured in response to the user's gait is transmitted to a terminal device installed in the hospital which the user visits. The gait information $I_g$ is displayed on the screen of the terminal device viewed by the doctor who can examine a symptom of the user. The doctor who has viewed the screen of the terminal device inputs action recommendation information $I_r$ for the user to the terminal device based on the gait information $I_g$ of the user. The action recommendation information $I_r$ input to the terminal device is transmitted to the mobile terminal 280 of the user.

In the example of FIG. 17, the action recommendation information such as "Please visit our hospital for orthopedic consultation" is displayed on the screen of the mobile terminal 280. The user who has checked the action recommendation information displayed on the screen of the mobile terminal 280 can take an action according to his/her gait information by taking an action according to the action recommendation information.

Operation

Next, an operation of the gait measurement system 2 according to the present example embodiment will be described with reference to the drawings. Hereinafter, an operation of the gait information generation device 25 included in the gait measurement system 2 will be described. Since the operation of the sensor data measurement device 20 is similar to that of the sensor data measurement device 10 of the first example embodiment, the description thereof will be omitted.

Gait Information Generation Device

Figure 18:
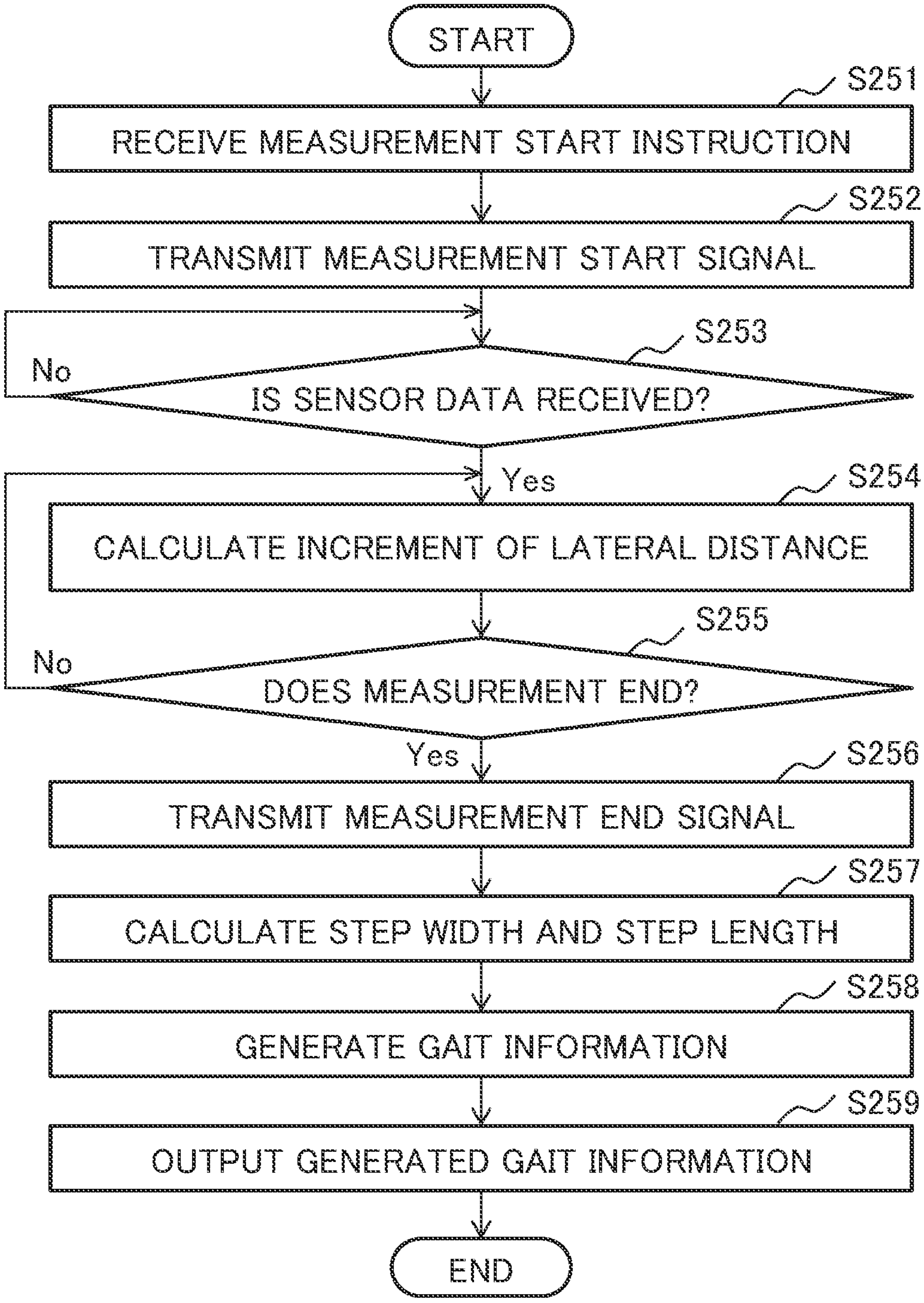
FIG. 18 is a flowchart for explaining an operation of a gait information generation device included in a gait measurement system according to the present disclosure.

FIG. 18 is a flowchart for explaining an example of an operation of the gait information generation device 25. In the description based on the flowchart of FIG. 18, components of the gait information generation device 25 will be described as main operation entities. A main operation entity of a process according to the flowchart of FIG. 18 may be the gait information generation device 25.

In FIG. 18, first, the measurement instruction acquiring unit 250 receives the measurement start instruction input by the user (step S251).

Next, the communication unit 251 transmits the measurement start signal to the sensor data measurement device 20 (step S252).

Next, when the communication unit 251 receives the sensor data (Yes in step S253), the increment calculating unit 252 calculates the increment of the lateral distance (step S254). When the communication unit 251 has not received the sensor data (No in step S253), the process is on standby until the sensor data is received.

After step S254, the determining unit 253 determines whether the measurement is ended (step S255). When the determining unit 253 determines that the measurement is ended (Yes in step S255), the communication unit 251 transmits the measurement end signal to the sensor data measurement device 20 (step S256). When the determining unit 253 determines that the measurement is not ended (No in step S255), the process of step S254 is continued.

After step S256, the gait information generating unit 255 calculates the step width and the step length (step S257).

Next, the gait information generating unit 255 generates the gait information related to the step width and the step length (step S258).

Next, the output unit 257 outputs the gait information related to the calculated step width and the step length (step S259). For example, the gait information related to the step width and the step length is output to the mobile terminal 280 carried by the user. For example, the gait information related to the step width and the step length is displayed on the screen of the mobile terminal 280. For example, the gait information related to the step width and the step length is output to a system that executes a process that uses the gait information.

As described above, the gait measurement system of the present example embodiment includes the sensor data measurement device and the gait information generation device. The sensor data measurement device is installed on the user's footwear. The sensor data measurement device includes the sensor including the acceleration sensor that measures the accelerations in three axial directions and the angular velocity sensor that measures the angular velocities around the three axes. The sensor data measurement device outputs the sensor data based on the physical quantities measured by the acceleration sensor and the angular velocity sensor to the gait information generation device.

The gait information generation device includes the communication unit, the increment calculating unit, the determining unit, the gait information generating unit, and the output unit. The communication unit acquires the sensor data measured in response to the motion of the foot. The increment calculating unit calculates the increment of the lateral distance using the lateral acceleration included in the sensor data. The determining unit determines the measurement end of the sensor data in response to the increment of the lateral distance. When it is determined that the measurement is ended in response to the increment of the lateral distance, the determining unit outputs the calculation instruction signal for giving an instruction to calculate the gait parameters including the step width. The gait information generating unit executes the calculation of the gait parameters including the step width in response to the calculation instruction signal. The gait information generating unit calculates, as the step width, the sum of the heel center distance substantially equivalent to the distance between the center lines of the heels of both feet in the initial state and the sum total of the increments of the lateral distance. The gait information generating unit performs second-order integral on the acceleration in the traveling direction included in the sensor data, and calculates the loci in the traveling direction. The gait information generating unit calculates the step length by using the calculated loci in the traveling direction. The gait information generating unit generates the gait information related to the calculated step width and step length. The output unit outputs the generated gait information.

The gait information generation device of the present example embodiment calculates the step width by using the lateral acceleration included in the sensor data measured in response to the motion of the foot. The gait information generation device of the present example embodiment calculates the step length by using the acceleration in the traveling direction included in the sensor data. The gait information generation device of the present example embodiment generates the gait information related to the calculated step width and step length. According to the technique of the present example embodiment, it is possible to generate the gait information related to the step width and the step length as long as it is possible to acquire the sensor data measured by the sensor installed in the footwear. That is, according to the present example embodiment, it is possible to generate the gait information related to the step width and the step length with a simple configuration.

Third Example Embodiment

Next, a gait information generation device according to a third example embodiment will be described with reference to the drawings. The gait information generation device of the present example embodiment has a configuration in which the gait information generation device included in the gait measurement system according to the first or second example embodiment is simplified.

Configuration

Figure 19:
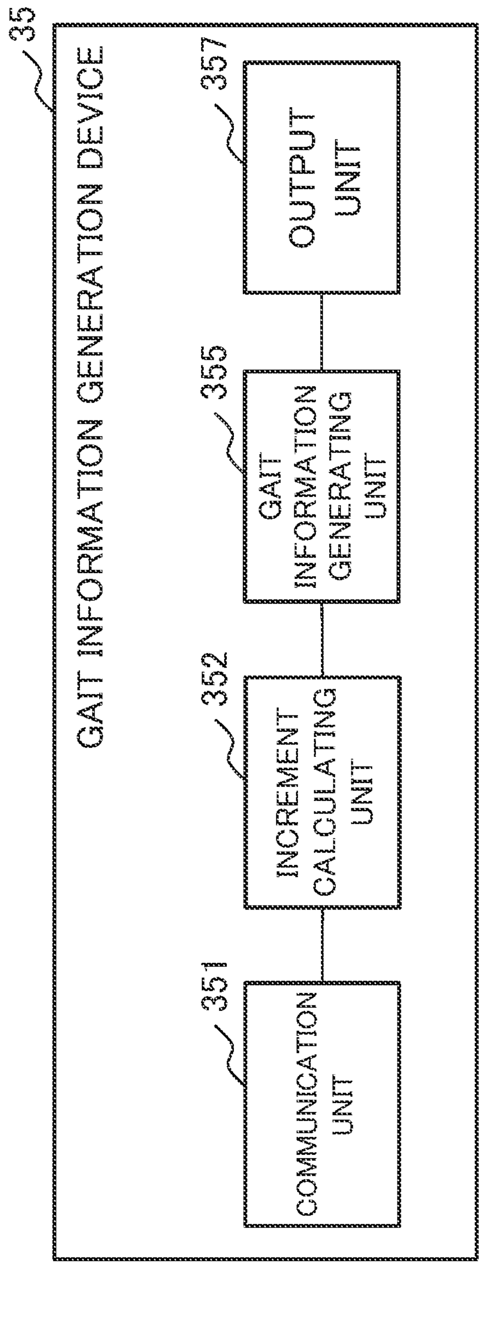
FIG. 19 is a block diagram illustrating an example of a configuration of a gait information generation device included in a gait measurement system according to the present disclosure.

FIG. 19 is a block diagram illustrating an example of a configuration of a gait information generation device 35 according to the present example embodiment. The gait information generation device 35 includes a communication unit 351, an increment calculating unit 352, a gait information generating unit 355, and an output unit 357.

The communication unit 351 acquires the sensor data measured in response to the motion of the foot. The increment calculating unit 352 calculates the increment of the lateral distance using the lateral acceleration included in the sensor data. The gait information generating unit 355 calculates, as the step width, the sum of the heel center distance substantially equivalent to the distance between the center lines of the heels of both feet in the initial state and the sum total of the increments of the lateral distance. The gait information generating unit 355 generates the gait information related to the calculated step width. The output unit 357 outputs the generated gait information.

Operation

Figure 20:
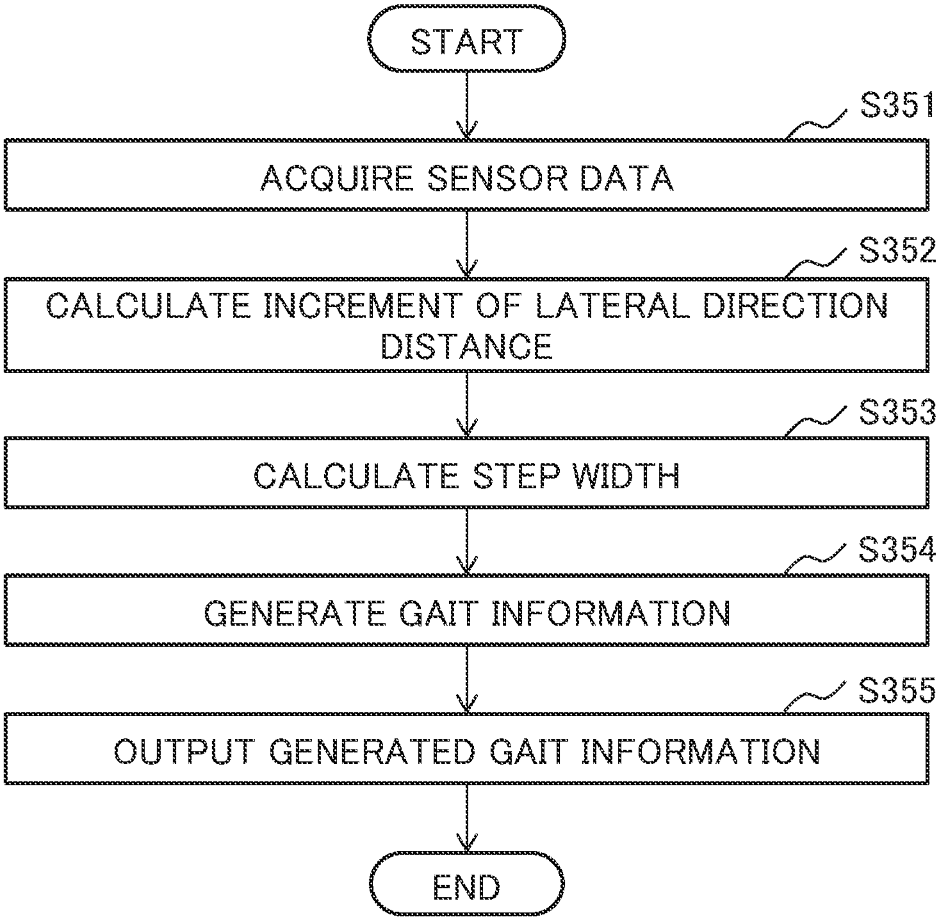
FIG. 20 is a flowchart for explaining an operation of a gait information generation device included in a gait measurement system according to the present disclosure.

FIG. 20 is a flowchart for explaining an operation of the gait information generation device 35 according to the present example embodiment. In the description of the process according to the flowchart of FIG. 20, components of the gait information generation device 35 will be described as main operation entities. A main operation entity of a process according to the flowchart of FIG. 20 may be the gait information generation device 35. For example, the process (gait information generation method) according to the flowchart of FIG. 20 is executed by a computer.

In FIG. 20, first, the communication unit 351 acquires the sensor data measured in response to the motion of the foot (step S351). The increment calculating unit 352 calculates the increment of the lateral distance using the lateral acceleration included in the sensor data (step S352). The gait information generating unit 355 calculates, as the step width, the sum of the heel center distance substantially equivalent to the distance between the center lines of the heels of both feet in the initial state and the sum total of the increments of the lateral distance (step S353). Next, the gait information generating unit 355 generates the gait information related to the calculated step width (step S354). Next, the output unit 357 outputs the generated gait information (step S355).

The gait information generation device of the present example embodiment generates the gait information related to the step width by using the lateral acceleration included in the sensor data measured in response to the motion of the foot. According to the technique of the present example embodiment, it is possible to generate the gait information related to the step width as long as it is possible to acquire the sensor data measured by the sensor installed in the footwear. That is, according to the present example embodiment, it is possible to generate the gait information related to the step width with a simple configuration.

Hardware

Next, a hardware configuration for executing control or processes according to each of the example embodiments of the present disclosure will be described with reference to the drawings. Here, an information processing device 90 (computer) of FIG. 21 will be described as an example of the hardware configuration. The information processing device 90 on FIG. 21 is a configuration example for executing control or processes of each of the example embodiments and not intended to limit the scope of the present disclosure.

Figure 21:
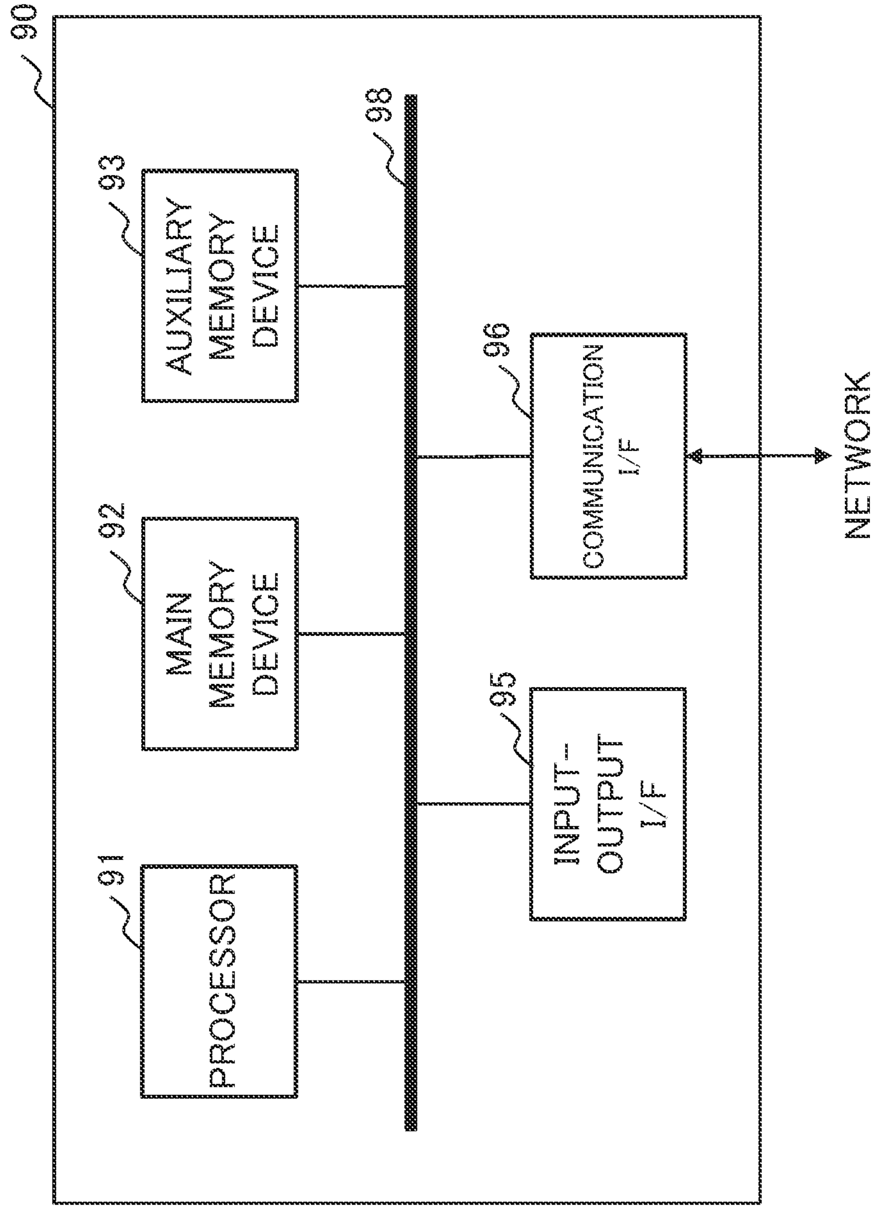
FIG. 21 is a block diagram illustrating an example of a hardware configuration that executes a process and control according to the present disclosure.

As illustrated in FIG. 21, the information processing device 90 includes a processor 91, a main memory device 92, an auxiliary memory device 93, an input-output interface

95, and a communication interface 96. In FIG. 21, the interface is abbreviated as I/F. The processor 91, the main memory device 92, the auxiliary memory device 93, the input-output interface 95, and the communication interface 96 are connected to one another via a bus 98 in such a way that data communication can be performed. The processor 91, the main memory device 92, the auxiliary memory device 93, and the input-output interface 95 are connected to a network such as the Internet or an intranet via the communication interface 96.

The processor 91 causes a program (instruction) stored in the auxiliary memory device 93 or the like to be developed in the main memory device 92. For example, the program is a software program for executing control or processes of each of the example embodiments. The processor 91 executes the program developed in the main memory device 92. The processor 91 executes the program in such a way that control or processes according to each of the example embodiments is executed.

The main memory device 92 has an area in which a program is developed. A program stored in the auxiliary memory device 93 or the like is developed in the main memory device 92 by the processor 91. The main memory device 92 is implemented by, for example, a volatile memory such as a dynamic random access memory (DRAM). A non-volatile memory such as a magneto resistive random access memory (MRAM) may be configured/added as the main memory device 92.

The auxiliary memory device 93 stores various pieces of data such as programs. The auxiliary memory device 93 is implemented by a local disk such as a hard disk or a flash memory. In a case in which various pieces of data are stored in the main memory device 92, the auxiliary memory device 93 may be omitted.

The input-output interface 95 is an interface for connecting the information processing device 90 with a peripheral device based on a standard or a specification. The communication interface 96 is an interface for connecting to an external system or device via a network such as the Internet or an intranet based on a standard or a specification. The input-output interface 95 and the communication interface 96 may be combined as an interface connected to an external device.

Input devices such as a keyboard, a mouse, and a touch panel may be connected to the information processing device 90 as necessary. These input devices are used to input information or settings. In a case in which a touch panel is used as the input device, a screen having a touch panel function serves as an interface. The processor 91 and the input devices are connected to each other via the input-output interface 95.

The information processing device 90 may be provided with a display device for displaying information. In a case in which the display device is provided, the information processing device 90 includes a display control device (not illustrated) for controlling display of the display device. The information processing device 90 and the display device are connected to each other via the input-output interface 95.

The information processing device 90 may be provided with a drive device. The drive device mediates reading of data or a program stored in a recording medium or writing of a processing result of the information processing device 90 in the recording medium between the processor 91 and the recording medium (program recording medium). The information processing device 90 and the drive device are connected to each other via an input-output interface 95.

The example of the hardware configuration for enabling control or processes according to each of the example embodiments of the present disclosure has been described above. The hardware configuration of FIG. 21 is an example of the hardware configuration for executing control or processes according to each of the example embodiments and not intended to limit the scope of the present disclosure. A program for causing a computer to execute control or processes according to each of the example embodiments is also included in the scope of the present disclosure.

A program recording medium in which the program according to each of the example embodiments is recorded is also included in the scope of the present disclosure. The recording medium can be implemented by, for example, an optical recording medium such as a compact disc (CD) or a digital versatile disc (DVD). The recording medium may be implemented by a semiconductor recording medium such as a universal serial bus (USB) memory or a secure digital (SD) card. The recording medium may be implemented by a magnetic recording medium such as a flexible disk or other recording media. In a case in which the program executed by the processor is recorded in the recording medium, the recording medium is substantially equivalent to the program recording medium.

The components of each of the example embodiments may be arbitrarily combined. The components of each of the example embodiments may be implemented by software. The components of each of the example embodiments may be implemented by a circuit.

The previous description of embodiments is provided to enable a person skilled in the art to make and use the present invention. Moreover, various modifications to these example embodiments will be readily apparent to those skilled in the art, and the generic principles and specific examples defined herein may be applied to other embodiments without the use of inventive faculty. Therefore, the present invention is not intended to be limited to the example embodiments described herein but is to be accorded the widest scope as defined by the limitations of the claims and equivalents.

Further, it is noted that the inventor's intent is to retain all equivalents of the claimed invention even if the claims are amended during prosecution.

The invention claimed is:

1. A gait information generation device, comprising:

a memory storing instructions, and a processor connected to the memory and configured to execute the instructions to:

receive, via wireless communication, sensor data measured by sensors installed in footwear of a user in response to a motion of a foot, the sensor data including lateral acceleration and acceleration in a traveling direction measured by an acceleration sensor;

calculate lateral distances of the left foot and the right foot by performing a second-order integral on the lateral acceleration;

calculate an increment of a lateral distance as a difference between the lateral distances of both feet;

determine a measurement end of the sensor data when the increment of the lateral distance becomes smaller than a preset reference measurement end value;

in response to determining the measurement end:

determine a total lateral step distance by calculating a sum total of the increments of the lateral distance; and calculate, as a step width, a sum of (i) a heel center distance that is a distance between center lines of heels of both feet in an initial state and (ii) the total lateral step distance;

generate gait information related to the calculated step width; and output the generated gait information to a mobile terminal of the user for display on a screen of the mobile terminal to enable the user to improve gait stability.

2. The gait information generation device according to claim 1, wherein the processor is configured to execute the instructions to calculate the difference between the lateral distances for each step of both feet as the increment of the lateral distance.

3. The gait information generation device according to claim 2, wherein the processor is configured to execute the instructions to determine a measurement end of the sensor data in response to the increment of the lateral distance, output a calculation instruction signal for giving an instruction to calculate gait parameters including the step width when it is determined that measurement is ended in response to the increment of the lateral distance, and calculate the gait parameters including the step width in response to the calculation instruction signal.

4. The gait information generation device according to claim 3, wherein the processor is configured to execute the instructions to determine that the measurement is ended when the increment of the lateral distance becomes smaller than a preset reference measurement end value.

5. The gait information generation device according to claim 1, wherein the processor is configured to execute the instructions to calculate loci in a traveling direction by performing second-order integral on an acceleration in a traveling direction included in the sensor data, calculate a step length by using the calculated loci in the traveling direction, and generate the gait information related to the calculated step length.

6. The gait information generation device according to claim 1, wherein the gait information is configured to be generated by machine learning, and includes information used for decision making according to the step width.

7. A gait measurement system, comprising:

the gait information generation device according to claim 1; and a data measurement device that is installed in footwear of a user and includes sensors including an acceleration sensor that measures acceleration in three axial directions and an angular velocity sensor that measures angular velocities around three axes, and outputs sensor data based on physical quantities measured by the acceleration sensor and the angular velocity sensor to the gait information generation device.

8. The gait measurement system according to claim 7, wherein the processor of the gait information generation device is configured to execute the instructions to acquire a measurement start signal generated by tapping a measurement start button displayed on a screen of a mobile terminal of the user, and transmit the acquired measurement start signal to the sensor data measurement device, the sensor data measurement device is configured to start measurement of the sensor data in response to the measurement start signal, and transmit the measured sensor data to the gait information generation device, the processor of the gait information generation device is configured to execute the instructions to determine a measurement end in response to the increment of the lateral distance, and transmit a measurement end signal to the sensor data measurement device when it is determined that the measurement is ended, and the sensor data measurement device is configured to end the measurement of the sensor data in response to the measurement end signal.

9. A gait information generation method causing a computer to execute:

receiving, via wireless communication, sensor data measured by sensors installed in footwear of a user in response to a motion of a foot, the sensor data including lateral acceleration and acceleration in a traveling direction measured by an acceleration sensor;

calculating lateral distances of the left foot and the right foot by performing a second-order integral on the lateral acceleration;

calculating an increment of a lateral distance as a difference between the lateral distances of both feet;

determining a measurement end of the sensor data when the increment of the lateral distance becomes smaller than a preset reference measurement end value;

in response to determining the measurement end:

determining a total lateral step distance by calculating a sum total of the increments of the lateral distance; and calculating, as a step width, a sum of (i) a heel center distance that is a distance between center lines of heels of both feet in an initial state and (ii) the total lateral step distance;

generating gait information related to the calculated step width; and outputting the generated gait information to a mobile terminal of the user for display on a screen of the mobile terminal to enable the user to improve gait stability.

10. A non-transitory recording medium having a program stored therein, the program causing a computer to execute:

a process of receiving, via wireless communication, sensor data measured by sensors installed in footwear of a user in response to a motion of a foot, the sensor data including lateral acceleration and acceleration in a traveling direction measured by an acceleration sensor;

a process of calculating lateral distances of the left foot and the right foot by performing a second-order integral on the lateral acceleration;

a process of calculating an increment of a lateral distance as a difference between the lateral distances of both feet;

a process of determining a measurement end of the sensor data when the increment of the lateral distance becomes smaller than a preset reference measurement end value;

in response to determining the measurement end:

a process of determining a total lateral step distance by calculating a sum total of the increments of the lateral distance; and a process of calculating, as a step width, a sum of (i) a heel center distance that is a distance between center lines of heels of both feet in an initial state and (ii) the total lateral step distance;

a process of generating gait information related to the calculated step width; and a process of outputting the generated gait information to a mobile terminal of the user for display on a screen of the mobile terminal to enable the user to improve gait stability.

* * * * *